United States Patent
Besio et al.

(10) Patent No.: US 8,190,248 B2
(45) Date of Patent: May 29, 2012

(54) MEDICAL DEVICES FOR THE DETECTION, PREVENTION AND/OR TREATMENT OF NEUROLOGICAL DISORDERS, AND METHODS RELATED THERETO

(75) Inventors: Walter G. Besio, Ruston, LA (US); Mohammed Fasiuddin, San Diego, CA (US); Ravish Patwardhan, Shreveport, LA (US)

(73) Assignees: Louisiana Tech University Foundation, Inc., Ruston, LA (US); Board of Supervisors of Louisiana State University, Shreveport, LA (US)

( * ) Notice: Subject to any disclaimer, the term of this patent is extended or adjusted under 35 U.S.C. 154(b) by 1247 days.

(21) Appl. No.: 11/252,043

(22) Filed: Oct. 17, 2005

(65) Prior Publication Data

US 2006/0173510 A1  Aug. 3, 2006

Related U.S. Application Data

(63) Continuation-in-part of application No. 10/967,891, filed on Oct. 18, 2004, now abandoned.

(60) Provisional application No. 60/511,914, filed on Oct. 16, 2003.

(51) Int. Cl.
*A61N 1/00* (2006.01)
*A61B 5/04* (2006.01)

(52) U.S. Cl. ............... 600/544; 600/545; 607/45

(58) Field of Classification Search ............ 607/45, 607/67, 139, 148; 600/393, 544–545
See application file for complete search history.

(56) References Cited

U.S. PATENT DOCUMENTS

| | | | |
|---|---|---|---|
| 6,016,449 A * | 1/2000 | Fischell et al. | 607/45 |
| 7,006,859 B1 * | 2/2006 | Osorio et al. | 600/378 |
| 7,010,351 B2 * | 3/2006 | Firlik et al. | 607/45 |
| 7,221,981 B2 * | 5/2007 | Gliner | 607/116 |
| 7,305,268 B2 * | 12/2007 | Gliner et al. | 607/45 |
| 2003/0050673 A1 | 3/2003 | Yamazaki et al. | |
| 2003/0187490 A1 | 10/2003 | Gliner | |
| 2004/0102828 A1 | 5/2004 | Lowry et al. | |
| 2004/0158298 A1 | 8/2004 | Gliner et al. | |

FOREIGN PATENT DOCUMENTS

JP  2001/271203 A  10/2001
WO  WO 03/089057 A1  10/2003

OTHER PUBLICATIONS

European Patent Office Communication enclosing the Extended European Search Report for EP 05808963, dated May 11, 2010.

* cited by examiner

*Primary Examiner* — Mark W Bockelman
(74) *Attorney, Agent, or Firm* — Clark & Elbing LLP; Kristina Bieker-Brady

(57) ABSTRACT

Disclosed are devices and methods for detecting, preventing, and/or treating neurological disorders. These devices and methods utilize electrical stimulation, and comprise a unique concentric ring electrode component. The disclosed methods involve the positioning of multiple electrodes on the scalp of a mammal; monitoring the mammal's brain electrical patterns to identify the onset of a neurological event; identifying the location of the brain electrical patterns indicative of neurological event; and applying transcutaneous or transcranial electrical stimulation to the location of the neurological event to beneficially modify brain electrical patterns. The disclosed methods may be useful in the detection, prevention, and/or treatment of a variety of indications, such as epilepsy, Parkinson's Disease, Huntington's disease, Alzheimer's disease, depression, bipolar disorder, phobia, schizophrenia, multiple personality disorder, migraine or headache, concussion, attention deficit hyperactivity disorder, eating disorder, substance abuse, and anxiety. The disclosed methods may also be used in combination with other peripheral stimulation techniques.

16 Claims, 9 Drawing Sheets

MEDICAL DEVICES FOR THE DETECTION, PREVENTION AND/OR TREATMENT OF NEUROLOGICAL DISORDERS, AND METHODS RELATED THERETO

CROSS REFERENCE TO RELATED APPLICATIONS

This is a continuation-in-part application claiming the benefit of and priority to provisional patent application Ser. No. 60/511,914 filed on Oct. 16, 2003, and non-provisional application Ser. No. 10/967,891 filed on Oct. 18, 2004, both of which are incorporated by reference.

TECHNICAL FIELD

The present invention relates generally to medical devices, more specifically, to medical devices for the detection, prevention, and/or treatment of neurological disorders, and methods related thereto.

BACKGROUND

Epilepsy is one of several neurological disorders that can be severely debilitating and/or dangerous. Epilepsy is characterized by the occurrence of seizures, in particular episodic impairment, loss of consciousness, abnormal motor phenomena, psychic or sensory disturbances. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Traditional treatment modalities for epilepsy are moderately efficacious; however, they suffer from several severe drawbacks. One such technique for controlling epilepsy involves the use of dopaminergic agonists or anticholinergic agents. Managing epilepsy using this technique requires iterations in dosing adjustments to balance efficacy and side effects. A number of drugs are approved and available for treating epilepsy, such as lorazopan, diazapan, sodium valproate, phenobarbital/primidone, ethosuximide, gabapentin, phenytoin, and carbamazepine, among others. Unfortunately, these drugs typically have serious side effects, especially toxicity. Further, it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects that the patient may wish to avoid. Moreover, while many epilepsy patients respond well to drug therapy alone, a significant number (at least 20%-30%) do not. For those patients, surgery is presently the best-established and most viable alternative course of treatment.

Commonly practiced surgical approaches for medically refractory epilepsy include surgical resection, such as hemispherectomy, corticectomy, lobectomy and partial lobectomy, and less-radical lesionectomy, transection, and stereotactic ablation. Surgery is not always completely successful and generally has a risk of complications. Further, surgery can result in damage to eloquent (i.e., functionally important) brain regions and the consequent long-term impairment of various cognitive and other neurological functions. Surgical treatments are contraindicated in a substantial number of patients for various reasons. Moreover, of those epilepsy patients who do undergo surgery, many are still not seizure-free after surgery.

Another traditional approach for controlling epilepsy is tissue ablation. Tissue ablation is typically performed via stereotactic neurosurgical procedures, including pallidotomy, thalamotomy, subthalamotomy, and other lesioning procedures. These procedures are only moderately efficacious.

Tissue ablation procedures not only pose inherent surgical risks, but they also suffer from a number of fundamental limitations. One obvious limitation is irreversibility of tissue removal or destruction. Thus, any excessive or inadvertent removal of tissue is final.

Electrical stimulation is an emerging method for treating epilepsy. However, currently approved and available electrical stimulation devices apply continuous electrical stimulation to neural tissue surrounding or near implanted electrodes, and do not perform any detection—simply they do not respond to relevant neurological conditions. One example of an electrical stimulation device is the NeuroCybernetic Prosthesis (NCP) from Cyberonics, Inc. The vagus nerve stimulator (VNS) of this device, for example, applies continuous electrical stimulation to the patient's vagus nerve. The VNS has been found to reduce seizures by about 50% in about 50% of patients tested. Still, a much greater reduction in the incidence of seizures is necessary to provide substantial clinical benefit. Even though the VNS may change the electrical pattern of a seizure, and increasing the interictal time may allow eventual seizure control, some studies in the literature suggest that quality of life is dependent upon the frequency of seizures and not necessarily the interictal time. Hence, the ultimate goal of any antiepileptic therapy should not simply be the facilitation of seizure reduction via changing the seizure pattern or increasing interictal time, but should be actually stopping the seizures.

Electrical stimulation has also been utilized for the treatment of other neurological disorders. For example, a commercially available product, the Activa deep brain stimulator, from Medtronic, Inc., is a pectorally implanted continuous deep brain stimulator intended primarily to treat Parkinson's disease. This device supplies continuous electrical pulses to a selected deep brain structure where an electrode has been implanted in a predetermined neurological region. Chronic high frequency intracranial electrical stimulation is typically used for inhibiting cellular activity in an attempt to functionally mimic the effect of tissue lesioning. Acute electrical stimulation to neural tissue, and electrical recording and impedance measurement from neural tissue are methods commonly used in the identification of brain structures, such as target localization, during neurosurgical operations for the treatment of various neurological disorders.

Continuous stimulation of deep brain structures for the treatment of epilepsy has not met with consistent success. To be effective in terminating seizures, it is believed that stimulation should be performed near the focus of the epileptogenic region. The focus is often in the neocortex, where continuous stimulation may cause significant neurological deficit with clinical symptoms, including loss of speech, sensory disorders, or involuntary motion. Alternatively, the focus of general seizures may move and would thus require insertion of electrodes where the focus moves. This, as well as other conventional treatment modalities, offer some benefit to patients with epilepsy; however, their efficacy is often limited.

Accordingly, research has also been directed toward automatic responsive epilepsy treatment based on a detection of imminent seizure. Neuropace, Inc. is presently developing and conducting clinical trials on an implantable responsive neurostimulator for epilepsy. Once again, there are the risks involved with an implantable system. For episodes where the focus of the seizure moves, or where there is no clear focus, it would be nearly impossible to place electrodes in every location where a seizure focus may be. Compromises must be made to minimize the number of implanted electrodes and maximize the efficacy. Another major concern is that such a device cannot be implanted quick enough during an emergency seizure that is pharmaco-resistant.

Trigeminal nerve stimulation is also a possible method for desynchronizing seizure activity. Advanced Bionics, Inc. is currently developing an implantable device for the treatment of epilepsy that involves the application of electrical stimulation to the trigemnial nerve. As with the vagus nerve, the trigeminal nerve does not project to all areas of the brain and cannot stop all seizures. Once again, this method will have the same concerns for implantable devices as with the above-mentioned devices.

There has been only one anecdotal report in the literature about electroconvulsive therapy (ECT) use in medically intractable seizures in human patients (Griesemer et al., Neurology; 1997 49(5):1389-92): one patient experienced "change in a seizure pattern with cessation at higher intensity," while the other experienced "decrease in spontaneous seizure frequency". Surprisingly, no further studies to investigate this methodology in an animal model or in a human clinical series are found. Electroconvulsive therapy (ECT) is performed using conventional EEG electrodes that are not capable of focusing stimulation to a specific volume of biological tissue. To perform ECT, strong muscle relaxants, as well as sedation, are often used. Thus, the patient must be monitored closely.

It has been proposed that if one can apply electrical stimulation at or near the foci, the origin of epileptiform activity, the efficacy of seizure control will be increased. Finding the seizure foci usually involves very expensive and immobile imaging equipment, such as a functional magnetic resonance (fMRI) system. Even with such an elaborate system, real-time analysis of the seizure activity still cannot be achieved. Another means for seizure foci localization is to drill holes into the cranium, and insert electrodes to record and analyze the electrical activity from the brain to determine the location of the foci. The latter technique is extremely invasive, requires a neurosurgeon, and can lead to complications. Similar techniques are applicable for the treatment of Parkinson's disease and other neurological disorders. Another problem that neither of these techniques can overcome is that the foci may move to various other locations. The fMRI and other similar imaging systems, such as positron emission tomography (PET), depend on blood flow changes, which can take many seconds to minutes to occur and thus unable to capture images of fast changing brain activity. A moving seizure focus is at best difficult to map with electrodes inserted into the brain; it may take many electrodes and many holes in the cranium to track the moving foci.

The use of electroencephalogram (EEG) is another approach to epilepsy therapy. EEG is a method for recording brain electrical activity non-invasively from the scalp surface. It can have very good temporal resolution, less than 1.0 ms per sample. EEG can also be a portable system and without being exceedingly expensive. However, EEG does have its limitations, such as the difficulty of localizing, with the type of electrodes used, the sources within the brain due to the smoothing affects of the skull and other body tissue.

There are various methods disclosing localizing mechanisms of biological electrical activity. They all involve post processing of data acquired from either disc or bipolar electrodes. Post processing involves either comparing simulated and measured potentials iteratively, or using a bank of software filters. The solution for source localization by these methods is not in real time, and the use of MRI/CT data is often necessary. In one example, magnetoencephalographic (MEG) is used to localize sources in the brain (see e.g., U.S. Pat. No. 6,697,660). It has high temporal resolution similar to EEG, however, it is very costly, not portable, and requires a special room to facilitate its use.

In another example, multiple spatial filters are used for the localization of electrical sources from EEG signals in the brain (see e.g., U.S. Pat. No. 5,263,488). This technique requires post processing and is limited in resolution due to the use of conventional EEG electrodes.

In another example involving the localization of electrical sources in the brain using EEG, (MRI another method of imaging the head is used for determining the shape and thickness of the scalp, skull, cerebrospinal fluid, and brain (see e.g., U.S. Pat. No. 5,331,970). Once this information is acquired, then a computer model is developed and a mathematical deblurring algorithm is applied to estimate the location of the sources on the cortical surface of the brain. This requires much post processing time to determine where the sources originate from and cannot be used in real-time.

A similar approach has been utilized for imaging electrical activity of the heart (see e.g., U.S. Pat. No. 6,856,830). This method involves the recording of ECG on the body surface, obtaining an MRI or CT image of the patient's torso, and entering both components into a heart-torso model. The ext step of this method involves post processing, whereby, the body surface potentials are calculated for sources in the heart and compared to the measured body surface potentials. This procedure must be repeated iteratively until the two components are within a given preset error range. Hence, this process cannot be performed in real-time. Further, there is no definite localization of the sources, and, distortion, due to global sources, is evident because the recording is performed with ordinary ECG electrodes.

In another example, regular EEG recording techniques and/or MEG are used, and restrictions are placed on the location where the brain electrical activity may be occurring (see e.g., U.S. patent application 20030093004). This approach is limited by the fact that the location of the activity must be known prior to the performance of this technique in order for this type of a system to resolve an inverse localization from the surface potentials. Further, this technique suffers from the blurring effects of the heads volume conductor.

In another example, electrical impedance plethysmography (EIP) is suggested for localizing electrical sources inside biological tissue (see e.g., U.S. patent application 20020038095). In EIP, impedance characterizations that are made over a period of time are used to localize changes in the body tissue. Electrical stimulation is injected into tissue and return signals are measured to determine the impedance. As sources below the surface interact with the injected signals, a map of conductivities is developed, and a model is assembled from these conductivities to iteratively localize sources in the tissue. This type of device is still dependent on typical EEG electrodes, which accept global signals distorting the localization process.

As the current approaches to therapy, which include systems that are presently available and those that are under development, such as drugs, surgery and implantable systems, present a variety of complications, there is a need for a system and method to non-invasively detect, treat, and prevent neurological disorders, particularly epilepsy.

SUMMARY OF THE INVENTION

Electroconvulsive therapy is currently utilized for the treatment of various disorders, such as depression. However, ECT, as well as other methods of therapy, such as drug therapy and implantable systems, that are currently being used for the treatment of various neurological disorders present a variety of complications that limit their successful use and standardization of therapy.

In view of the above, there is a need for a minimally invasive medical device that can detect, prevent and/or treat neurological disorders. Preferably, such a device will involve electrical stimulation, as this approach shows great potential to achieve the desired results. It is also desirable to have detection, prevention, and/or treatment methods that are safe and effective, short in duration, and are non- or minimally invasive.

It is, therefore, an object of the present invention to provide such a medical device for the detection, prevention, and/or treatment of neurological disorders that can yield the desired results in a safe and consistent manner.

It is another object of the present invention to provide such a medical device that is an electrical stimulator and feedback device, utilizing a unique electrode system for discriminating different electrical sources in a body's volume conductor by direct measurement of brain electrical activity.

It is another object of the present invention to provide such a medical device that is capable of enhancing localization of sources.

It is another object of the present invention to provide methods for the detection, prevention, and/or treatment of neurological disorders.

It is yet another object of the present invention to provide a method for detecting, preventing, and/or treating seizures via the application of electrical stimulation.

It is a further object of the present invention to provide such methods that are safe and effective, with minimal invasion, and that have short treatment periods.

The present invention pertains to medical devices for the detection, prevention, and/or treatment of neurological disorders, based on electrical stimulation. In one embodiment of the present invention, such a device comprises a unique electrode system that can discriminate different electrical sources in a body's volume conductor by direct measurement of brain electrical activity. Preferably, the electrode comprises at least one outer conductive element and one central conductive element, with the outer conductive element(s) surrounding the central conductive element, and thereby forming a concentric configuration. This concentric ring electrode possesses very high global signal attenuation, which enhances the localization process. The electrode's conductive elements may be arranged in a concentric geometric configuration of a ring, a square, a rectangle, an ellipse, or a polygon comprising any number of sides. The electrodes are fabricated from a metal, a non-metallic conductive material, or a combination thereof, wherein the metal or the non-metallic conductive material is biocompatible, or comprises a conductive biocompatible coating In one embodiment of the present invention, a bioelectric neuro device comprises a control module, one or more electrodes, and a power supply. The control module comprises a stimulation sub-system, a communication sub-system, and a central processing unit (CPU). A clock may be attached externally to the CPU or it may be integrated therein. The electrode arbiter comprises a steering logic controller and one or more electronic switches. The detection sub-system comprises one or more amplifiers, one or more analog-to digital (A/D) converters, and a digital signal processor (DSP). The impedance sub-system comprises one or more impedance signal generators and an impedance controller. The stimulation sub-system comprises one or more stimulation signal generators, a stimulation controller, and a high voltage supply.

In one embodiment of the present invention, wires from the electrodes are connected to electrode arbiter, and to detection and stimulation sub-systems. The wires carry signals, such as electroencephalogram (EEG) signals, from the electrodes to the electrode arbiter. The electrodes, attached to a portion of a patient, are stimulated by the stimulation sub-system via the electrode arbiter, whereby the electrodes become energized. The electrodes are preferably attached to the scalp of a patient by placement on or under the scalp, or anywhere in between the scalp and the brain, or anywhere within the brain. The attachment facilitates the stimulation of the brain.

The present invention also pertains to methods for the detection, prevention, and/or treatment of neurological disorders.

In one embodiment, the method involves the positioning of at least one two-element electrode on a portion of a mammal; monitoring brain electrical signal patterns of the mammal to identify the presence or onset of a neurological event; identifying the location of the brain electrical patterns indicative of neurological event prior to the applying of electrical stimulation; and; and applying electrical stimulation to beneficially modify the brain electrical patterns.

In one embodiment of the present invention, brain electrical signals directly localize at least two specific volumes of tissue via at least nine electrodes arranged in a specific configuration. In another embodiment, this direct localization is accomplished via a three-pole or greater concentric electrode configuration.

The methods of present invention involve the transcutaneous, transcranial, or a combination, application of electrical stimulation. The electrical stimulation may be applied in the form of sustained current, pulsed current, specific pulse pattern, sustained voltage, pulsed voltage, or any combination thereof. The frequency of electrical stimulation suitable for use herein is a in the range of from about 0.1 Hz to about 2500 Hz; the pulse width suitable for use herein is in the range of from about 10 μsec to about 10 sec, and the duration of stimulation suitable for use herein is in the range of from about 15 sec to about 30 min. The methods of the present invention involve the application of voltage in the range of from about 500 mV to about 2 kV, preferably from about 30 volts to about 100 volts, and current amplitudes in the range of from about 0.01 mA to about 1000 mA, preferably from about 5.0 mA to about 50 mA.

The methods of present invention also pertain to the use of the bioelectric neuro device to deliver electrical stimulation via concentric electrodes in combination with other peripheral stimulation techniques, such as drugs.

The bioelectric neuro device of the present invention, and methods related thereto may be minimally-invasive or, preferably, noninvasive.

The above summary of the present invention is not intended to describe each illustrated embodiment or every implementation of the present invention. The figures and the detailed description which follow particularly exemplify these embodiments.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF EXEMPLARY EMBODIMENTS

Figure 1:
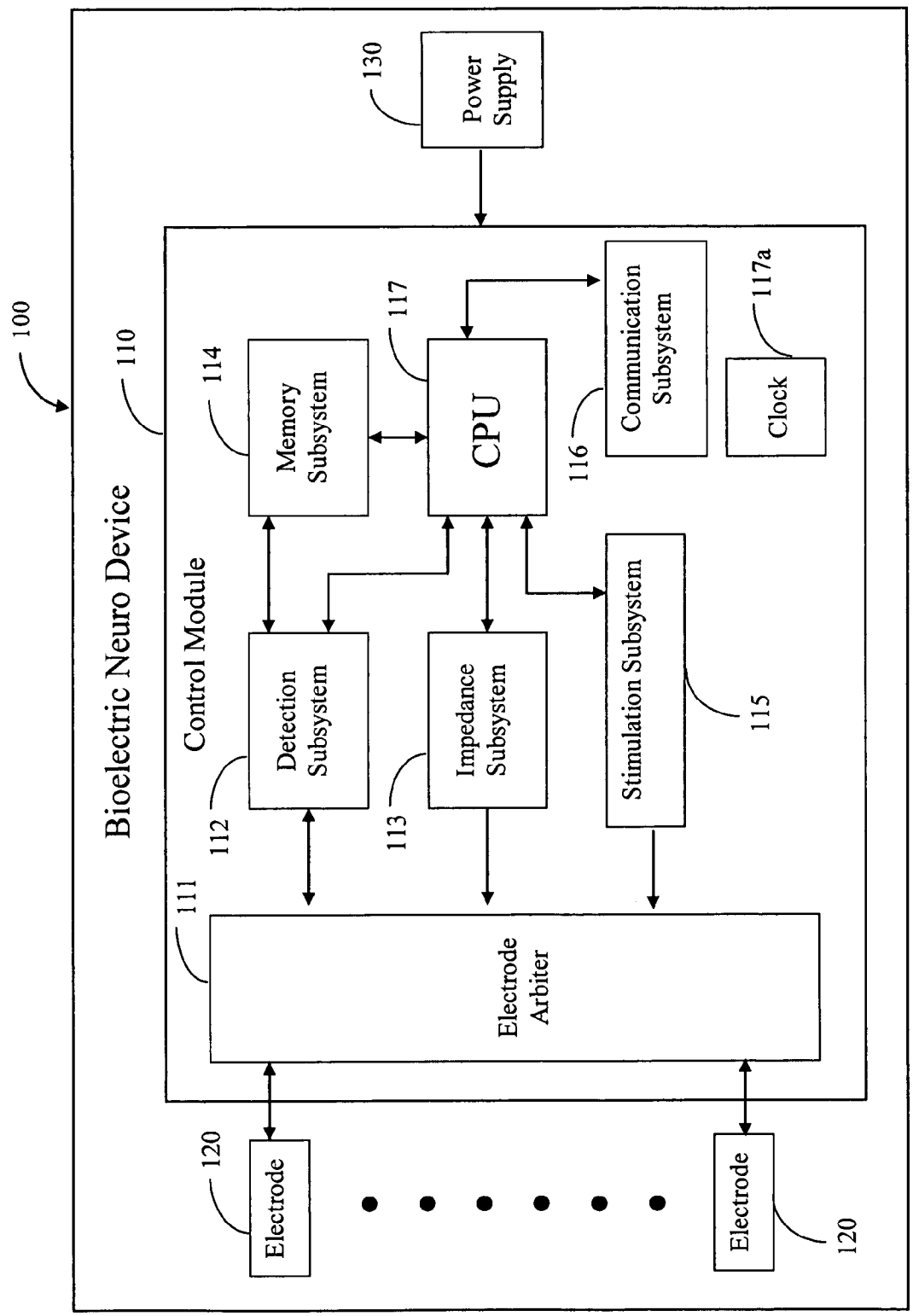
FIG. 1 schematically illustrates a control module of the bioelectric neuro device, according to an embodiment of the present invention.

The present invention pertains to medical devices for detecting, preventing, and/or treating neurological disorders, based on electrical stimulation. The present invention also pertains to methods for detecting, preventing, and/or treating neurological disorders utilizing such devices.

1. Definitions

The term "bioelectric neuro device", as used herein, refers to the medical device for the detection, prevention, and/or treatment of neurological disorders via electrical stimulation.

The term "concentric", as used herein, refers to electrode elements wherein larger elements surround the smaller elements. In a preferred embodiment, conductive elements configured as rings with consecutively increasing radius surround a central conductive disc. In other embodiments, the conductive elements that surround the central electrode element may be a square, rectangle, ellipse, or polygon comprising any number of sides.

The term "electrical source" or "electrical sources", as used herein, refers generally to neurons or nerves that generate electrical signals in the brain. However, man-made electrical sources, such as a deep brain stimulation, may also be contemplated here, as it may be desirable to localize such man-made sources.

The term "electrode", as used herein, refers to an electric conductor through which an electric current enters or leaves an electrolytic cell or other medium.

The term "Laplacian" is derived from the second derivative of a potential after its French inventor Pierre Laplace (1749-1827), and as used herein, refers to the second spatial derivative of a sensed electric potential measured by the concentric ring electrodes. The Laplacian increases the spatial frequencies. When used to stimulate, these concentric ring electrodes similarly allow the electric field to be focused more specifically into the tissue than typical electrodes.

The term "neurological disorder" or "neurological disorders", as used herein, refers to any disorder, disease, and/or syndrome due to or resulting from neurologic, psychiatric, psychologic, and/or cerebrovascular symptomology or origin. Neurological disorders include, but are not limited to, epilepsy or other another generalized or partial seizure disorder, Parkinson's Disease, Huntington's disease, Alzheimer's disease, Pick's disease, Parkinsonism, rigidity, hemiballism, choreoathetosis, dystonia, akinesia, bradykinesia, hyperkinesia, depression, bipolar disorder, anxiety, phobia, schizophrenia, multiple personality disorder, substance abuse, attention deficit hyperactivity disorder, eating disorder, impaired control of aggression, or impaired control of sexual behavior, headache, or chronic headache, migraine, concussion, post-concussive syndrome, stress-related disorder, or any combination thereof.

The term "neurological event", as used herein, refers to abnormal neural activity, such as a seizure, a migraine, or depression.

The term "stimulation", as used herein, refers to an electrical signal or signals applied to the scalp, to or near brain tissue, or to skin surface, such as on the face or neck.

The term "N", as used herein, refers to an indefinite quantity or duplications of some item, e.g., from 1 to N.

The term "sensitivity", used herein, refers to the ratio of the signal detected by an electrode from an electrical source directly below the center of the electrode, to the signal detected by an electrode from an electrode source not directly below the center of the electrode.

It is to be understood that the singular forms of "a", "an", and "the", as used herein and in the appended claims, include plural reference unless the context clearly dictates otherwise.

2. The Bioelectric Neuro Device

The medical device of the present invention, bioelectric neuro device 100, an embodiment of which is illustrated in FIG. 1, comprises a control module 110, one or more electrodes 120, and a power supply 130. The bioelectric neuro device 100 may further comprise external equipment for viewing signals, device controls and wires. Depending on the application, the medical device of the present invention may differ in its function and/or configuration. For example, for the detection, prevention, and/or treatment of seizures, such as epileptic seizures, the device may be a seizure stimulator or fibrillator; for treating depression, the device may be a depression stimulator, and etc. The seizure fibrillator's functions include detecting specific electrical activity due to or resulting from a neurological disorder, such as epilepsy. The depression stimulator's functions include the detecting of specific electrical signals due to or resulting from depression. Regardless of its intended application, this device comprises a unique concentric electrode design that can be used for direct depth detection of electrical sources, source location on a body surface, and high-resolution electrical signal detection. Accordingly, the bioelectric neuro device has the capability to locate the source of the originating electrical activity. Further, this device is capable of more specifically targeting areas and delivering more uniform stimulation than is possible with conventional electrodes, to ameliorate the neurological disorder quickly. The bioelectric neuro device is also capable of comparing the states before and after the application of stimulation to determine the necessity of further doses of stimulation. If it is determined that more stimulation is necessary, then the device is capable of applying further stimulation, and if it is determined that no more stimulation is necessary, then the device continues to analyze the electrical signals to determine if any future action is necessary.

Figure 2:
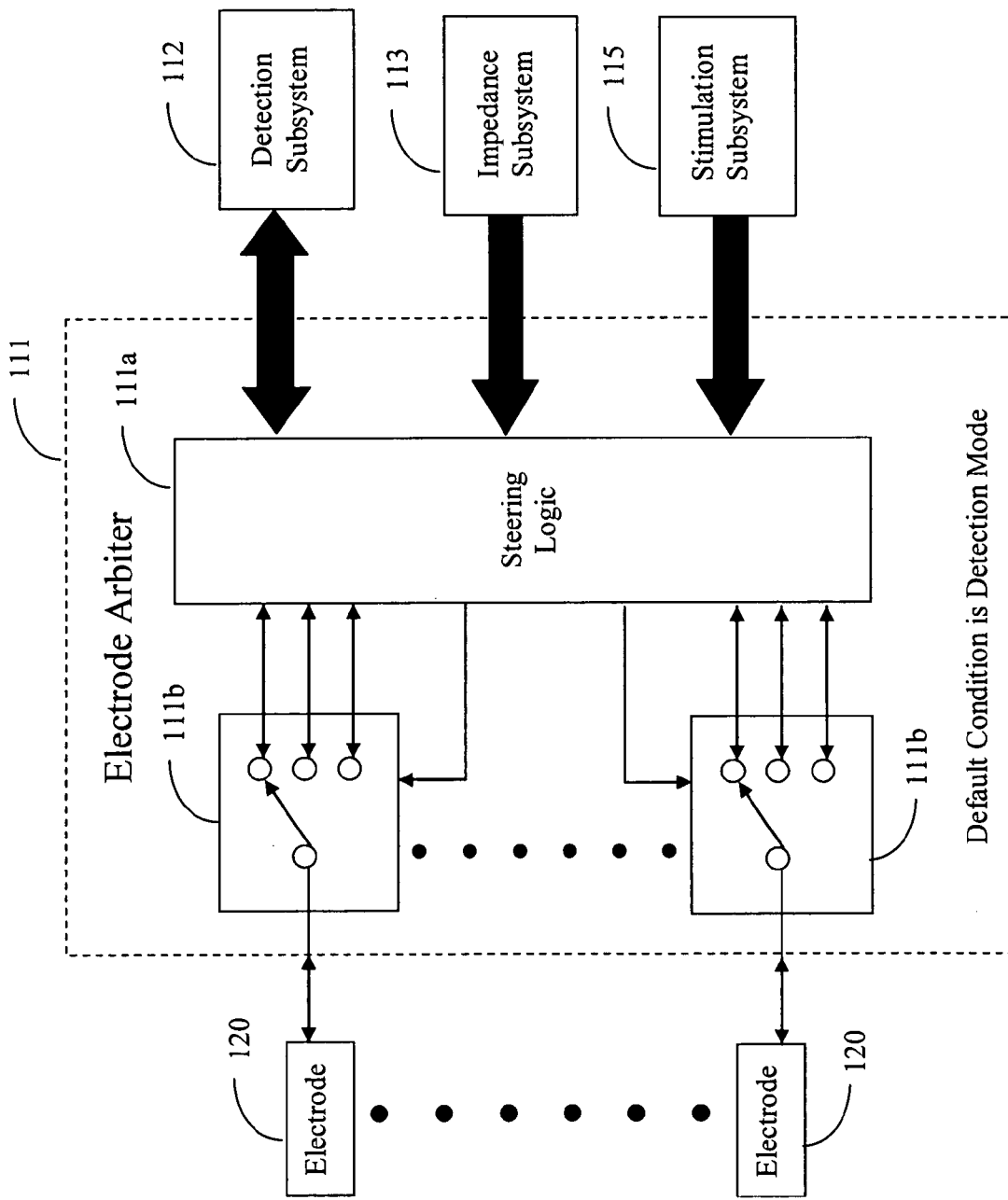
FIG. 2 schematically illustrates the electrode arbiter of the bioelectric neuro device and its connectivity to other device components, according to an embodiment of the present invention.
Figure 3:
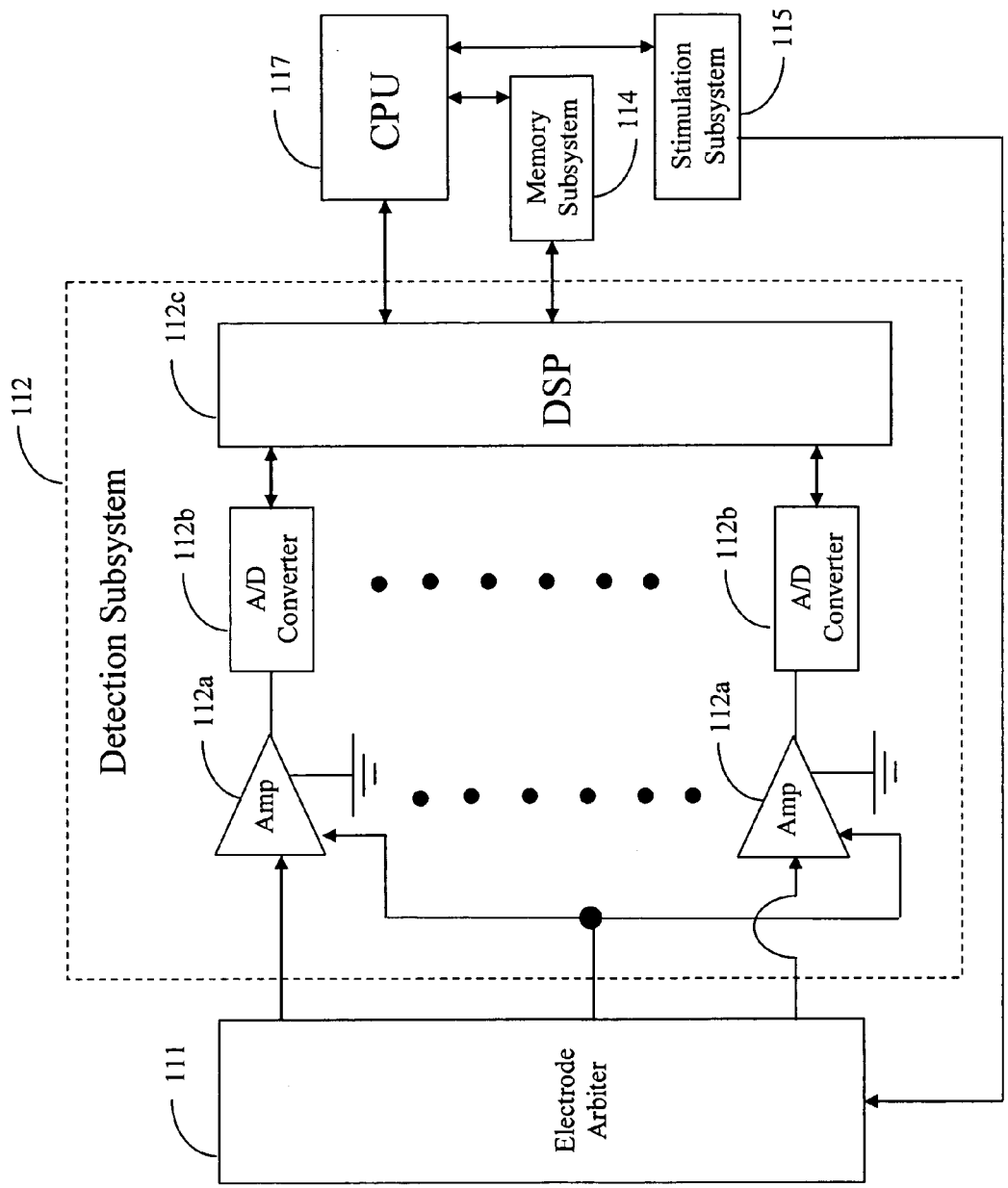
FIG. 3 schematically illustrates the detection sub-system of the bioelectric neuro device and its connectivity to other device components, according to an embodiment of the present invention.
Figure 6:
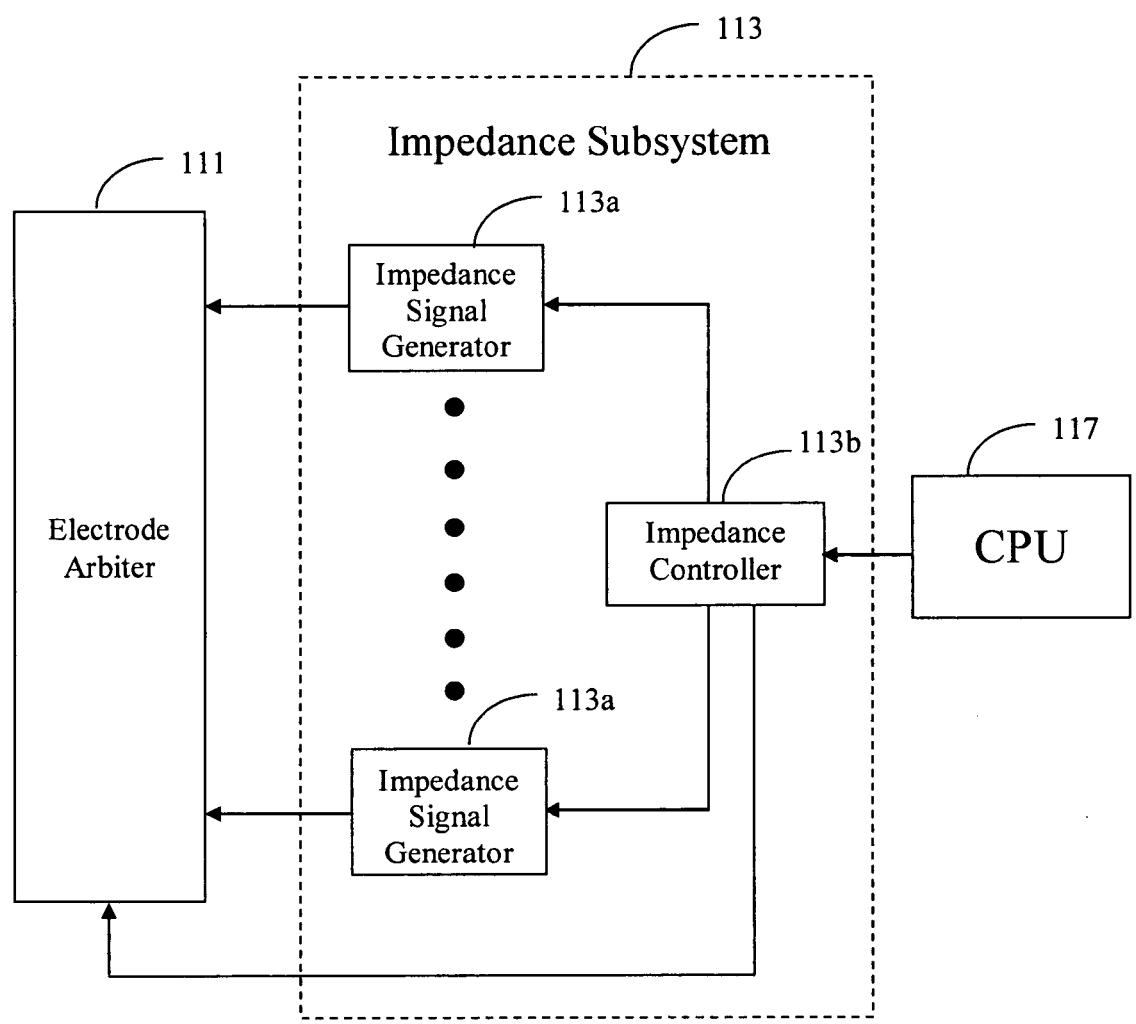
FIG. 6 schematically illustrates the impedance sub-system of bioelectric neuro device and its connectivity to other device components, according to an embodiment of the present invention.
Figure 7:
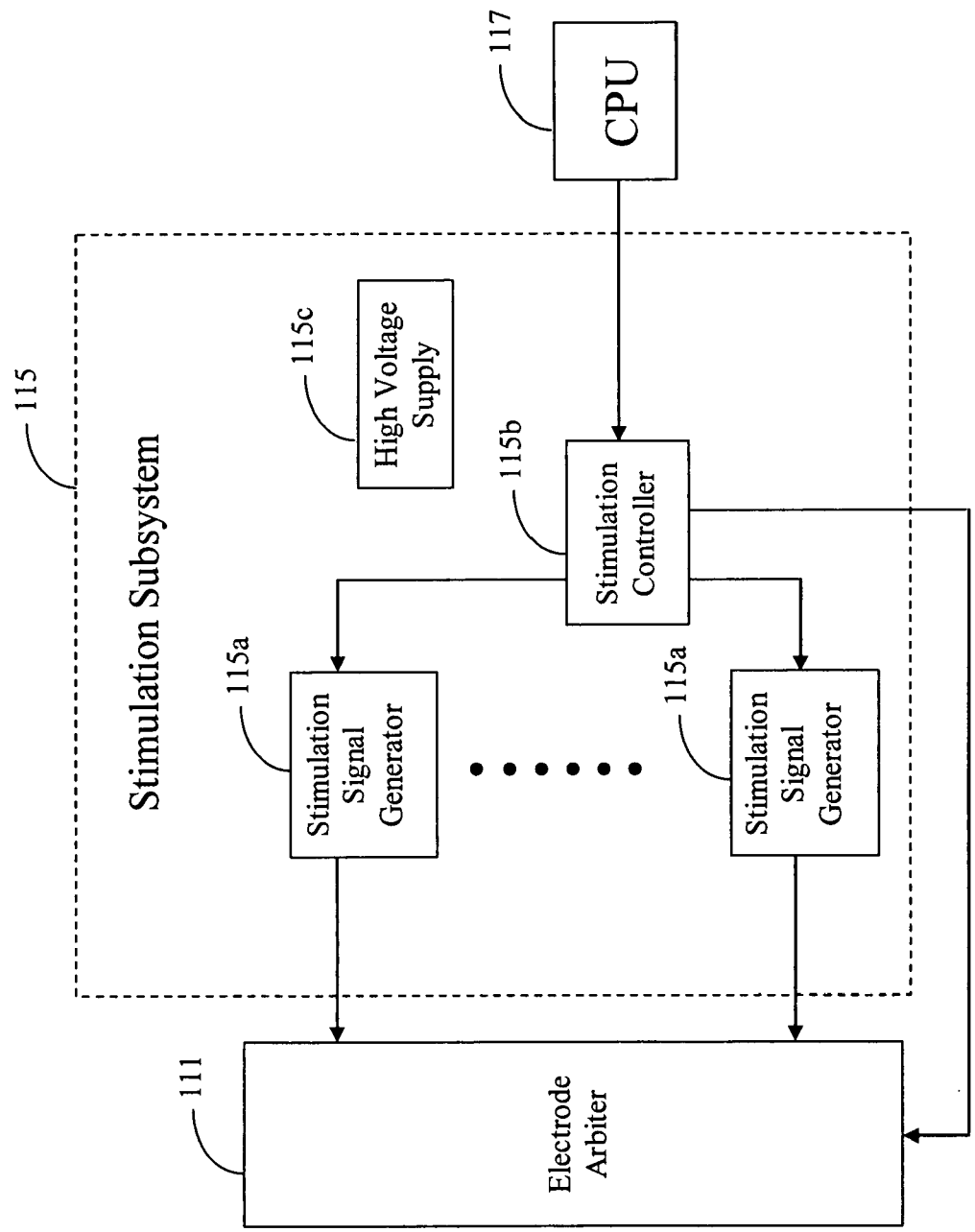
FIG. 7 schematically illustrates the stimulation sub-system of bioelectric neuro device and its connectivity to other device components, according to an embodiment of the present invention.

The control module 110 of the bioelectric neuro device comprises an electrode arbiter 111, a detection sub-system 112, an impedance sub-system 113, a memory sub-system 114, a stimulation sub-system 115, a communication sub-system 116, and a central processing unit (CPU) 117. A clock 117a may be attached externally to the CPU 117 or it may be integrated therein. The electrode arbiter 111, an embodiment of which is illustrated in FIG. 2, comprises a steering logic controller 111a and one or more electronic switches 111b. The detection sub-system 112, an embodiment of which is illustrated in FIG. 3, comprises one or more amplifiers 112a, one or more analog-to digital (A/D) converters 112b, and a digital signal processor (DSP) 112c. The impedance sub-system 113, an embodiment of which is illustrated in FIG. 6, comprises one or more impedance signal generators 113a and an impedance controller 113b. The stimulation sub-system 115, an embodiment of which is illustrated in FIG. 7, comprises one or more stimulation signal generators 115a, a stimulation controller 115b, and a high voltage supply 115c.

The analog-to-digital converter 112b, digital signal processor 112c, digital memory 114, central processing unit, which may be a microcomputer, 117, and amplifier 112a components used in the device of the present invention may be any such component that is known in the art or is commercially available. The techniques to interconnect these components and to program them may be any such technique known in the art. Alternatively, the present device may utilize custom very large scale integration (VLSI) or hybrid circuits that comprise any combination of these components or their functions.

In one embodiment of the present invention, wires from electrodes 120 are connected to electrode arbiter 111, and to detection sub-system 112 and stimulation sub-system 115, as shown in FIG. 1. The wires carry signals, such as electroencephalogram (EEG) signals, from electrodes 120 to electrode arbiter 111. The electrodes 120, attached to a patient's scalp, are stimulated by the stimulation sub-system 115 via the electrode arbiter 111, whereby the electrodes 120 inject currents into the patient. The electrodes 120 may be attached to the scalp by placement on or under the scalp, or anywhere in between the scalp and the brain, or anywhere within the brain. The attachment facilitates the stimulation of the brain. In another embodiment, a separate set of electrodes 120 and associated wires are utilized with each sub-system. In such a configuration, the inclusion of electrode arbiter 111 may not be necessary.

The bioelectric neuro device 100 of the present invention may be minimally-invasive or, preferably, noninvasive. This can be advantageous for a variety of reasons. For example, no surgical procedure would need to be performed to implant the device before it can be used. Thus, the device can be applied to the person very quickly in an emergency situation. Research shows that the sooner the action is taken to control seizures, the better the outcome. Further, no surgical procedure would be necessary to change the electrodes. The electrodes can be replaced easily as needed. The existing electrodes can also be replaced without any surgical procedures if a new electrode design is determined to be more efficacious. The location of the electrodes can also be changed without resorting to surgery. Only a reconfiguration of the electrode attachment mechanism may be necessary to accomplish this task, and it can be performed by a technician rather than a neurosurgical team. Moreover, batteries can be changed without the need for surgery. This task could be performed by anyone, such as a technician, rather than a neurosurgical team. These, and other such advantages, make the use of the bioelectric neuro device very cost-effective. One particular cost-effective aspect of this device is that one device can be used for treating multiple people, whereas an implantable device can only be used to treat one person. This can be particularly important from a medical standpoint, as it can be used in emergency situations to address the needs of many rather than just one.

2.1 The Detection Sub-System

The detection sub-system 112 of a bioelectric neuro device 100, such as a seizure fibrillator, serves to detect neurological events. The detection sub-system 112 automatically detects neurological events. In one embodiment of the present invention, the detection sub-system 112, as illustrated in FIG. 3, receives signals, e.g., EEG signals (referenced to the system ground), from the brain or other source, and processes them to identify a neurological event, such as an epileptic seizure or its precursor. The central processing unit (CPU) 117 and memory sub-system 114 act to control and coordinate all functions of the seizure fibrillator. The CPU 117 transmits programming parameters and instructions to the detection subsystem 112 via interconnections. The detection sub-system 112 transmits signals to the CPU 117 that identify the detection of a neurological event. The detection sub-system 112 can also transmit EEG and other related data into the memory sub-system 114 for storage. Currently available memory technology is suitable for EEG storage. For example, the EEG storage for a 42 electrode system using 16 bits (two bytes) per sample at a sampling rate of 500 samples per second (5 times over sampling of frequencies up to 100 Hertz (Hz)) will require 2,520,000 bytes per minute of data storage. Flash memory is commonly available in 256 megabyte devices that would allow approximately 100 minutes of data storage.

The detection sub-system 112 comprises one or more amplifiers 112a, one or more analog-to digital (A/D) converters 112b, and a digital signal processor (DSP) 112c. The amplifier 112a may comprise further signal processing circuitry, such as a bandpass filter. The bandpass filter can operate as a pre-filter to remove frequency components of a signal that is extraneous to or could interfere with the higher-level detection sub-system 112 components. Bandpass filters typically will limit low and high frequencies being transmitted. The bandpass filters that would be necessary for noninvasive application to the scalp surface may not use the same frequency parameters as those used by invasive devices. On the scalp surface, the skin-to-electrode contact may cause more low frequency artefact content than from implanted electrodes. Movement of the subject may also cause more low frequency artefacts than would be seen using invasive electrodes. For an external noninvasive device, it may be advantageous to set the high pass filter cutoff higher than for an invasive system. Typically, there is not much signal present in the electroencephalographic activity beyond 40 Hz. If the low pass filter is set for 40 Hz, then a 60 Hz or 50 Hz notch filter may not be necessary.

These components are preferably modular and may comprise discrete architecture, however, they may be integrated into a specialized integrated circuit due to space, power or cost considerations. The specialized integrated circuit may be a single mixed type, or a dual type containing one circuit for analog processing and one circuit for the digital conversion and processing. The detection sub-system 112 may exist as a stand-alone unit or it may be integrated with the electrodes, amplifiers 112a, stimulation sub-system 115, or any other component of the stimulator device.

The components of detection sub-system 112 can be placed in or on the body of a subject. For example, a detection sub-system 112 and other components of the seizure fibrillator, can be placed under the skin of a subject, making the seizure fibrillator entirely self-contained within the body of a subject.

Typically, electrical activity occurring in the brain of a subject (as recorded electroencephalographically) in the absence of any neurological events is normal and usually of a constant signal with little change in magnitude. During a neurological event, such as a seizure, the electrical activity is synchronized and has additive effect, causing higher or lower EEG than normal EEG.

In one embodiment, the detection sub-system 112 of a seizure fibrillator uses a signal that has been filtered by a band-pass filter in order to identify patterns of brain activity that characterize a neurological event. Such a detection sub-system 112 may employ any of a number of algorithms to identify a seizure. Such algorithms can be adapted to identify signal's components, which include, but are not limited to, the magnitude of the signal, the dominant frequency component of the signal, and time frequency analysis.

When a neurological event, such as a seizure, is detected by the detection subsystem 112, the CPU 117 can command the stimulation sub-system 115 to transmit electrical signals to any one or more of the electrodes 120 via the electrode arbiter 111 and wires. It is anticipated that, if appropriate electrical signals are transmitted to certain locations in, on, or near the brain, the normal progression of an epileptic seizure can be aborted. It may also be necessary for the stimulation sub-system 115 to temporarily disable the detection subsystem 112 when stimulation is imminent, via the electrode arbiter 111 so that the stimulation signals are not inadvertently interpreted as a neurological event by the detection sub-system 112 or damage the detection sub-system 112.

In another embodiment of the present invention, the detection sub-system 112 sends a signal to the (CPU and then the) stimulation sub-system 115 for a duration of time that a signal meets the requirements of a given neurological event, and to not send signals to the stimulation sub-system 115 when the neurological event-related brain activity ceases. That is, stimulatory signals are only sent when a neurological event is present and stimulatory signals are not sent when the EEG signals fall below the threshold value or do not meet a known pattern of a neurological event. Sending signals to the stimulation sub-system 115 only during periods in which neurological events are present may prevent side effects. Further, doing so may minimize or eliminate any potential damage or harm to the tissue.

Figure 4:
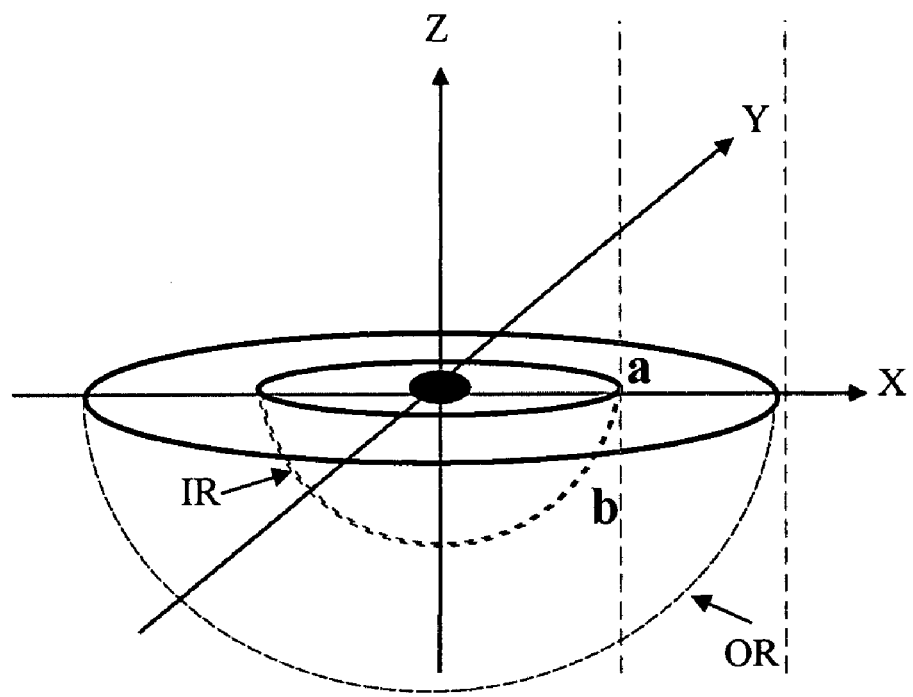
FIG. 4 schematically illustrates the configuration of tripolar concentric electrodes for directly detecting two depth volumes, according to an embodiment of the present invention.

The detection sub-system 112 is capable of directly detecting different depth sources to facilitate the localization of sources; this feature is integral to the unique electrode design. The different depth sources are detected based on the analysis of the lead field of a concentric disc and ring bipolar lead system. In such a system, the sensitivity drops off rapidly, $1/r^4$ for a dipole beyond the outer radius of the annulus (ring), and the sensitivity for locating radial dipoles reaches maximum at the gap between the disc and the ring. With a disc and two concentric rings around it, a tripolar electrode system can be viewed as two bipolar electrode systems: the disc and the smaller ring forming one bipolar system, and the disc and the larger ring forming a second bipolar system. When an electrical source is located outside of the area of the disc and smaller ring, but inside the area encompassed by the larger ring, such as at the point "a" in FIG. 4, the signal detected by the disc and smaller ring bipolar system is attenuated drastically by $1/r^4$, while the signal for the disc and larger ring bipolar system is not. The potential measured by the larger electrode would be more than that for the smaller electrode. If the source is within the radius of the smaller electrode, the potential measured by the smaller electrode would be larger than the potential of the larger electrode. Therefore, each disc and ring bipolar system is spatially selective to sources within the reach of their radii. If additional larger rings are continued to be included, the area over which the electrode system can localize electrical sources continues to be extended.

The source need not be on the plane of the electrodes. The same concept is applicable for depth detection. In this way, specific depth ranges can be determined. Consider a source below the plane of the electrode, such as at the point "b" in FIG. 4. Its distance to the center of the disc is outside the radius of the smaller ring bipolar electrode (IR), but inside the radius of a larger ring bipolar electrode (OR). Therefore, the signal detected by the disc and the smaller ring bipolar electrode is attenuated drastically by $1/r^4$, while the signal for the outer, larger ring is not. The outer ring potential would be greater than that of the disc and middle ring difference potential. Alternatively, if the dipole is within the radius of the middle ring, the disc and middle ring difference potential would be greater than that of the outer ring.

Figure 5:
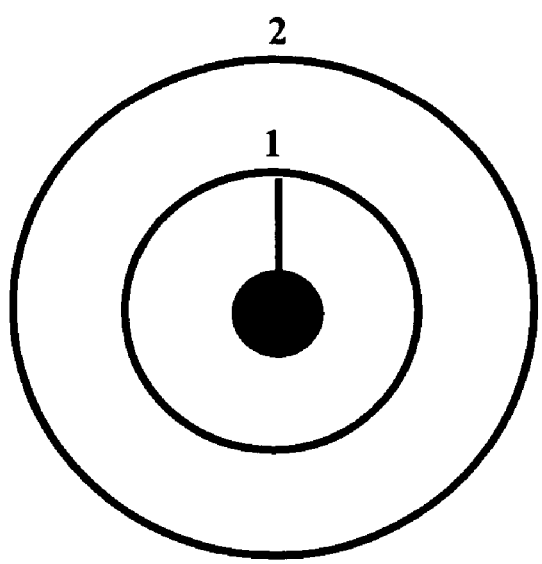
FIG. 5 schematically illustrates the configuration of a tripolar concentric electrode to perform a pseudo-bipolar difference, according to an embodiment of the present invention.

Direct localization of sources to specific volumes of tissue or to other medium can be achieved with the unique concentric electrode configuration of the present device, and may also be achieved with specific configurations of conventional electrodes. This unique feature performs significantly better with concentric electrodes than with conventional electrodes because concentric electrodes discriminate global sources more so than conventional electrodes. This global attenuation feature limits noise originating from beyond the outer distance of the concentric electrode. The hardware, i.e., the electrodes and circuitry, provides bipolar difference signals from the electrodes 120 controlled by the detection sub-system 112 to the digital signal processor 112c. These difference pairs are combinations of increasing electrode size. First, the difference between the potentials of the disc and the innermost ring is taken acquired in a bipolar arrangement [Disc-Ring(1)]; then the disc and the same ring are shorted together, as illustrated in FIG. 5, and the difference between the potentials of the next larger ring and the shorted combination is taken measured as [½(Disc+Ring(1))–Ring(2)]. The average potential for the shorted electrode elements is always used. This pseudo-bipolar difference method is applicable for any number of concentric elements. The pseudo-bipolar differences can be performed with electronic circuitry, or by taking differential inputs between the electrode elements and the reference electrode and combining the differential signals digitally with a software algorithm.

2.2 The Impedance Sub-System

The stimulation impedance sub-system 113 of the present invention is used to check the impedance between the skin and the electrode. Generally, signals are transmitted more effectively when the impedance is low. In one embodiment of the present invention, the impedance sub-system 113, as illustrated in FIG. 6, is utilized to check and verify that skin-to-electrode contact is made and maintained. If the skin-to-electrode contact becomes too high, signals are degraded in both directions, i.e., to detection and from stimulation. The impedance sub-system 113 generates signals of known magnitude and frequencies, and instructs the electrode arbiter 111 that specific electrode(s) 120 need to be tested for skin-to-electrode impedance. The impedance controller 113b determines which electrodes will be tested, and incorporates them in between stimulation waveforms or at the start of stimulation waveform sequences. The arbiter 111 routes the impedance testing signals to the specific electrode(s) 120 and the return path of the signals to the detection sub-system 112. The magnitude of the signal received is then compared to the magnitude of the signal sent, and from Ohm's Law, the real part of the skin-to-electrode impedance can be determined. At low frequencies suitable for use herein, such as from about 1 Hz to about 500 Hz, preferably from about 100 Hz to about 200 Hz, the skin-to-electrode impedance will primarily be a real resistive component. The stimulation sub-system 115 can also generate signals for use in impedance detection, however, this may cause complications due to the mismatch of stimulation signal generator specifications to the impedance detection application. For example, the stimulation sub-system 115 will typically apply stimulation in the milliamp range whereas the impedance testing circuitry requires microamp range currents. Further, the stimulation sub-system 115 may produce less complex stimulation waveforms than the impedance sub-system 113.

Implanted systems that are currently used may decline in efficacy over time, due too an increase in electrode impedance, which results from fibrotic encapsulation of the electrode. In one embodiment of the present invention, constant current stimulation is used. As the impedance changes, the magnitude of the stimulation current will remain the same, as will the efficacy.

2.3 The Electrode Arbiter

The stimulation electrode arbiter 111 of the present invention is a multiplexing mechanism. It is used to make or break contacts between electrode(s) and sub-systems, such as the stimulation sub-system. In one embodiment of the present invention, the electrode arbiter 111, as illustrated in FIG. 2, allows the signals to be steered to and from specific electrodes 120. If separate electrode(s) are used for recording and stimulation then an arbiter is not necessary. Each electrode 120 can be connected to the three sub-systems—detection, impedance, and stimulation. The electrode arbiter 111's steering logic takes commands from each of these sub-systems and determines which electrodes 120 to connect to which sub-system. For example, when the stimulation sub-system 115 wants to apply stimulation to specific electrodes 120 that have been determined to be overlying the area where a neurological event is originating from, the stimulation sub-system 115 commands the electrode arbiter 111 to connect it to those particular electrodes. The arbiter 111 signals the detection sub-system 111 that those electrodes 120 are about to be stimulated and are not connected to the detection sub-system 112. Other electrodes 120 may still be connected to the detection sub-system 112 to evaluate the effects of the stimulation on the neurological event while the stimulation is ongoing. For quick and consistent activation and deactivation, and to prevent switch bounce, electronic switches are utilized by the electrode arbiter 111. An array of connections mapping the various interconnections of the electrodes 120 is possible with this electronic mechanism.

2.4 The Stimulation Sub-System

The stimulation sub-system 115 of the present invention may be initiated manually or automatically. Stimulation parameters may be inputted or programmed manually, or resident stimulation parameters may be used automatically.

In one embodiment of the present invention, FIG. 7 illustrates the stimulation sub-system 115, including its interconnections to other sub-systems. The stimulation sub-system 115 is used to stimulate the scalp, brain, or other biological tissue in response to a detected neurological event. The preferred embodiment of the stimulation sub-system 115 comprises a stimulation controller and N stimulation signal generators connected to the electrodes 120 through wires via the electrode arbiter 111. The event detection signal from the CPU 117 is received by the stimulation controller, which first sends a signal via the link to the electrode arbiter 111 to disconnect specific electrode(s) 120 from the detection sub-system 112 and to prepare for possible stimulation artefact during stimulation. The stimulation controller will then feed stimulation command signals to the stimulation signal generator(s) for a specific pre-programmed time period. The stimulation command signals may be simultaneous or may have a relative delay with respect to each other. These delays can be downloaded by the instruction and parameter download from the CPU 117. It may be desirable that the delays be adjusted so that the stimulation signals from the stimulation signal generators reach the neurological event focus in the brain at the same time and in-phase. Doing so may enhance performance of the stimulation subsystem 115 in turning off a neurological event. Alternately, experience may indicate that certain signals being out of phase when they arrive at the neurological event focus may be particularly efficacious in aborting a neurological event.

The stimulation command signals can be used to control the amplitude, waveform, frequency, phase and time duration of the stimulation signal generators' output signals, or any combinations of. Different stimulation parameters can be applied to different electrode(s) 120, and thereby allowing interference patterns to be generated. The stimulation controller can also have several patterns of stimulation pre-programmed to run automatically when triggered by the CPU 117 after a neurological event is detected, or the CPU 117 may be used to dictate the stimulation parameters. Such a preset stimulation pattern may include several stimulation sequences with different frequencies, magnitudes and/or other combinations of stimulation parameters used for specific lengths of time.

The typical stimulation signals generated by the stimulation signal generators 115a are preferably biphasic (that is, with equal energy positive and negative of ground), with a typical frequency in the range of from about 10 Hz to about 250 Hz, although frequencies in the range of from about 0.1 Hz to about 2500 Hz may be effective. It is also envisioned that pure DC voltages may be used, although they are less desirable. If frequencies above 30 Hz are used, the stimulation signal generators could be capacitively coupled to the electrodes 120 to block the DC voltages. The typical width of the biphasic pulse is preferably between about 50 microseconds and about 500 microseconds, although pulse widths of about 10 microseconds to about 10 seconds may be effective for a particular patient. The pulse width of the positive and negative phases may be of different durations and/or magnitudes Typically, voltage is applied in the range of from about 30 volts to about 100 volts, and current amplitudes in the range of from about 5.0 milliamperes (mA) to about 50 mA. However, it may be necessary to use magnitudes above 2000 V if the skin-to-electrode impedance is high, e.g., 40,000 ohms or greater. The current may also be effective and safe below and above this typical range. Stimulation is applied for a duration of from about 15 seconds to as long as 30 minutes, preferably, from about 30 seconds to about 5 minutes.

Biphasic voltage (current) generation circuits are well known in the art of circuit design and need not be diagrammed here. Similarly, the programming code for enabling the stimulation controller to provide different command parameters to the stimulation signal generators is easily accomplished using well known programming techniques.

If the waveform parameter modulated by the stimulation controller control law is the stimulation voltage magnitude, the design would not benefit from the independence of impedance variation as controlling the stimulation current would allow. Alternatively, regulation of the stimulus pulse width may be desired. In certain circuit implementations, the available resolution or bits for specifying the magnitude of pulse width may be greater than that for specifying the pulse voltage or current. In such a case, if finer control of the magnitude of the stimulation is desired than is provided by the control of pulse current or pulse voltage, then it may be desirable to modulate the pulse width. Selection between regulation of pulse voltage, pulse current, or pulse width as the regulated pulse amplitude parameter is determined by the stimulation controller, which may be set using communication via the operator interface. In alternative embodiments, the modulation of pulse frequency and the modulation of the number of pulses per burst are regulated. Other such characteristics may be regulated in addition to or instead of the ones noted above.

In one embodiment, charge balanced biphasic waveforms are preferably produced. The net charge contained in a given pulse is determined by the time integral of the stimulus current over the duration of the pulse. In a biphasic configuration, a pair of pulses of opposite polarity is generated, and the pulse current amplitude and pulse width are chosen such that the charge amplitude is equal in magnitude and opposite in polarity. In some cases, it is desirable for the pulses comprising the biphasic pulse pair to have different amplitudes; in this case, the pulse widths are selected to insure equal and opposite charges such that the pulse pair introduces zero net charge to the biological tissue.

Although the waveform parameters of the pulse pairs are calculated to deliver a zero net charge, in practice, noise and precision limitations and nonlinearities in the digital to analog conversion and amplification stages may result in slight imbalances in the pulse pair charges. Over time, this can result in the delivery of a substantial accumulated net charge to the biological tissue. To eliminate this potential for net charge delivery to neural tissue, a direct current (DC) blocking capacitor is employed. This technique is well known in the art. In one preferred embodiment, a DC blocking capacitor is included in series with the stimulator output path.

It is also expected that by applying the stimulation from multiple sets of electrodes there will be a summation of intensity at the location where the stimulation is focused, a superposition affect. This will be beneficial because it will require less stimulation intensity from each set of electrodes, lowering the risk of tissue damage. Lowering the intensity will also lessen the chance of stimulating non-seizure affected areas of the brain.

The feedback control signal for the detector/stimulator combination is preferably but not limited to, an EEG signal, and/or EMG and EOG. While a neurological event is being detected, stimulation is applied. This is basically a proportional control. If stability and performance requirements dictate, other components, such as an integrator and/or a differentiator, may be added to the control law to produce a proportional-integral-differential (PID) controller.

A power supply provides power to each component of the device. Such a power supply typically utilizes a primary (rechargeable) storage battery with an associated DC to DC converter to obtain the necessary voltages as required by the bioelectric neuro device.

2.5 The Communication Sub-System

The communication sub-system 116 of the present invention may be used to enable external communication to and from the bioelectric neuro device. In one embodiment of the present invention, the bioelectric neuro device comprises radio telemetry-based components that can be employed to wirelessly transmit or download stored EEG signals, detection parameters, or other parameters, to a computer, a data storage, or analysis component or device. A new detection algorithm can also be downloaded into the detection sub-system 112 via radio telemetry or any other method.

In one embodiment, the data stored in the memory of the device is retrieved by a physician via a wireless communication link while the data communication sub-system is connected to the central processing system 117. Alternatively, an external data interface can be directly connected with an RS-232 type serial connection or USB connection to an external physician's or operator's workstation. Alternately, the serial connection may be via modem(s) and phone line from the patient's home, emergency vehicle, or a remote area to the physician's workstation. The software in the computer component of the physician's workstation allows the physician to obtain a read-out of the history of events detected, including EEG information before, during and after the neurological event, as well as specific information relating to the detection of the neurological event, such as spiking frequency of the patient's EEG. The workstation also allows the physician or operator to specify or alter the programmable parameters of the bioelectric neuro device. RF transceiver circuitry and antennas for this purpose are used widely in medical device data communication.

2.6 The Real-Time Clock Sub-System

A real time clock 117a, which is attached externally to the CPU 117 or integrated therein, is used for timing and synchronizing various portions of the bioelectric neuro device, and for enabling the device to provide the exact date and time corresponding to each neurological event detected by the device and recorded in memory. In one embodiment of the present invention, the CPU 117 sends data to the real-time clock 117a in order to set the correct date and time in the clock 117a.

2.7 The Concentric Electrode

The electrode 120 for use herein may be a surface electrode or an implantable electrode, with each type possibly having different physical and material properties. The electrode 120 may be soft, pliable, and flexible enough to conform to the tissue it is contacting, it may be stiff, or it may be any variation in between. The conductive electrode 120 may be fabricated from a variety of metals, such as gold, platinum, or iridium, nonmetals, such as conductive polymers or any combination thereof that are biocompatible or having conductive biocompatible coatings. Each electrode 120 has a multi-polar configuration, and comprises at least two conductive elements, although electrode embodiments having three elements, tripolar, are primarily disclosed herein. One or more conductive elements surround a central conductive element, such as a disc, in a concentric configuration. The width of the conductive elements can vary such that an increase in width inversely affects spatial resolution. The conductive elements are configured such that a gap is formed therebetween. The gap between the electrodes is preferably equal to the width of the conductive elements to ensure best approximation to the Laplacian. This gap may be adjusted to perform specific spatial filters, such as exponential filtering.

The many unique features of the bioelectric neuro device provides the medical device of the present invention with a variety of advantages. In one embodiment, the bioelectric neuro device performs automated determination of the treatment dosage. This dosage includes the selection of the number of electrodes for stimulation, electrode polarities, electrode configurations, stimulation frequencies, stimulating parameter waveforms, temporal profile of stimulation magnitude, stimulation duty cycles, baseline stimulation magnitude, intermittent stimulation magnitude and timing, and other stimulation parameters. This automation capability provides an added advantage to the bioelectric neuro device.

In one embodiment, the bioelectric neuro device provides signal processed sensory feedback signals to clinicians so as to assist their manual selection of optimum treatment magnitude and pattern. Sensory feedback signals provided to the clinician, via a clinician-patient interface include, but are not limited to, location of seizure foci, interictal rates, tremor estimates, EEG signals, and other signals.

In one embodiment, the unique concentric electrodes of the bioelectric neuro device allow for enhancement of the acquisition of local electrical signals, while sharply attenuating electrical signals from more distant sources.

In one embodiment, the unique concentric electrodes of the bioelectric neuro device directly measure the depth and surface location of electrical activity without other imaging modalities, such as CT, PET, MRI. This in particular is useful for localizing abnormal neurological sources. Once the sources have been localized, then they can be targeted with focused electrical stimulation.

In one embodiment, the concentric electrodes of the bioelectric neuro device are used for stimulation. The same benefit of enhancing detection of local electrical signals holds true when applying electrical stimulation, due to reciprocity. The stimulation can be focused to specific volumes of biological tissue (or other medium) with the use of the concentric electrodes.

In one embodiment, the bioelectric neuro device is used for applying electrical stimulation concurrently from multiple concentric electrodes that originate from different sites, and are directed at a particular location; the stimulation intensities will sum when their paths cross. Therefore, the stimulation intensity from individual electrodes can be reduced, and thereby increasing the safety factor.

Although the present disclosure describes medical devices having concentric ring electrodes, other electrode configurations, such as rectangles, ellipses, or polygons such as triangles or pentagons may also be utilized. However, the approximation to the Laplacian for such electrodes will be deteriorated. In some possible circumstances, it may be advantageous to utilize noncircular electrode configurations to perform spatial filtering of signals prior to the electronic acquisition, such as exponential or elliptical filtering.

Figure 8:
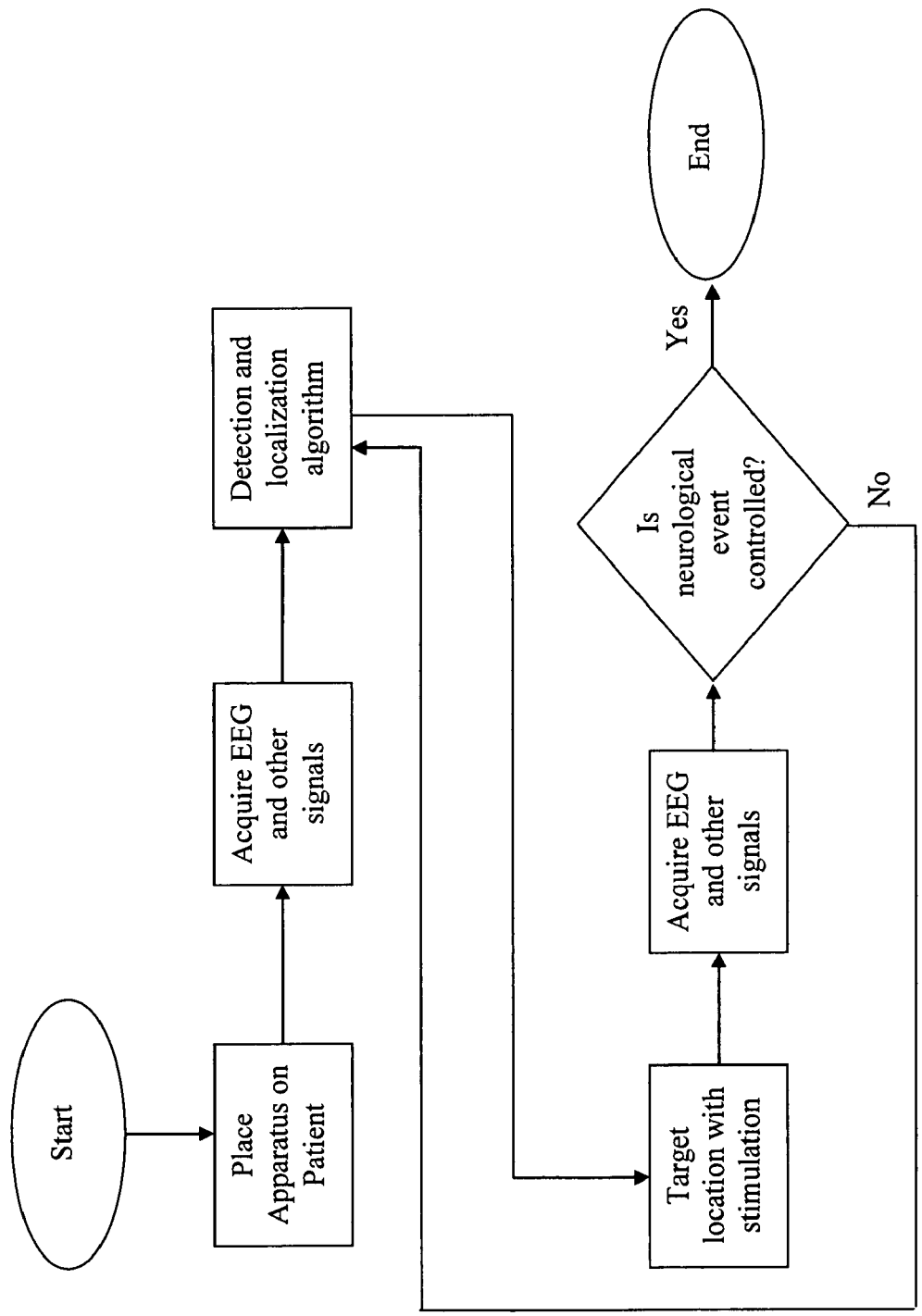
FIG. 8 is a flow chart of the methods for detection, localization, and/or treatment of neurological disorders, according to an embodiment of the present invention.
Figure 9:
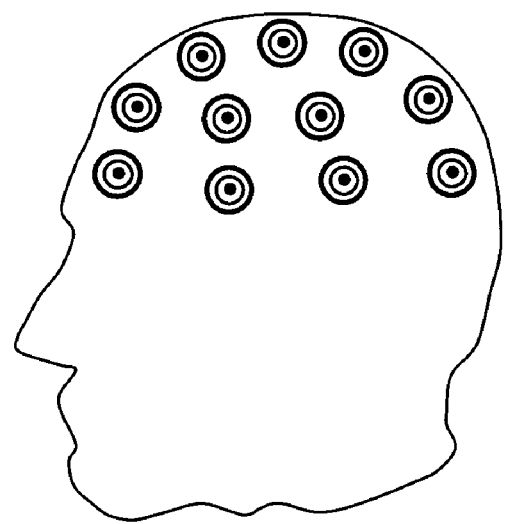
FIG. 9 schematically illustrates a subject's head with tripolar concentric electrodes placed thereon, according to an embodiment of the present invention.

3. Methods for the Detection, Prevention, and/or Treatment of Neurological Disorders The methods for detection, prevention, and/or treatment of neurological disorders using the bioelectric neuro device of the present invention are described hereinbelow. The flow chart in FIG. 8 illustrates the decision path used to effectuate these methods. The basic means of operation involves the system being placed on the subject, as illustrated in FIG. 9. In one embodiment, a neurological event is detected by the physician and verified by the detection sub-system 112.

In another embodiment, the detection sub-system 112 automatically detects the neurological event. Once the neurological event has been detected, the location of the origin of the neurological event is determined for events that have a specific origin, such as in epilepsy. Thereafter, electrical or other stimulation or a combination is applied to treat the neurological event. The signals are re-accessed to determine whether the neurological event has been controlled, if not then stimulation is re-applied. Each neurological event will have specific characteristics that will allow the detection sub-system to discriminate different neurological disorders, diseases, or syndromes using the same basic hardware but different detection algorithms and data bases for pattern matching. To prevent neurological events, the stimulation can be applied prior to a neurological event that has been predicted to occur or at intermittent intervals as needed. The details are described below.

3.1 Neurological Event Detection

Past work on the detection and responsive treatment of seizures via electrical stimulation has dealt with the analysis of EEG and electrocorticogram (ECoG) waveforms. In general, EEG signals represent aggregate neuronal activity potentials detectable via electrodes applied to a patient's scalp. ECoG signals, deep-brain counterparts to EEG signals, are detectable via electrodes implanted on or under the dura mater, and usually within a patient's brain. Unless the context clearly and expressly indicates otherwise, the term "EEG" shall be used generically herein to refer to both EEG and ECoG signals.

Figure 10:
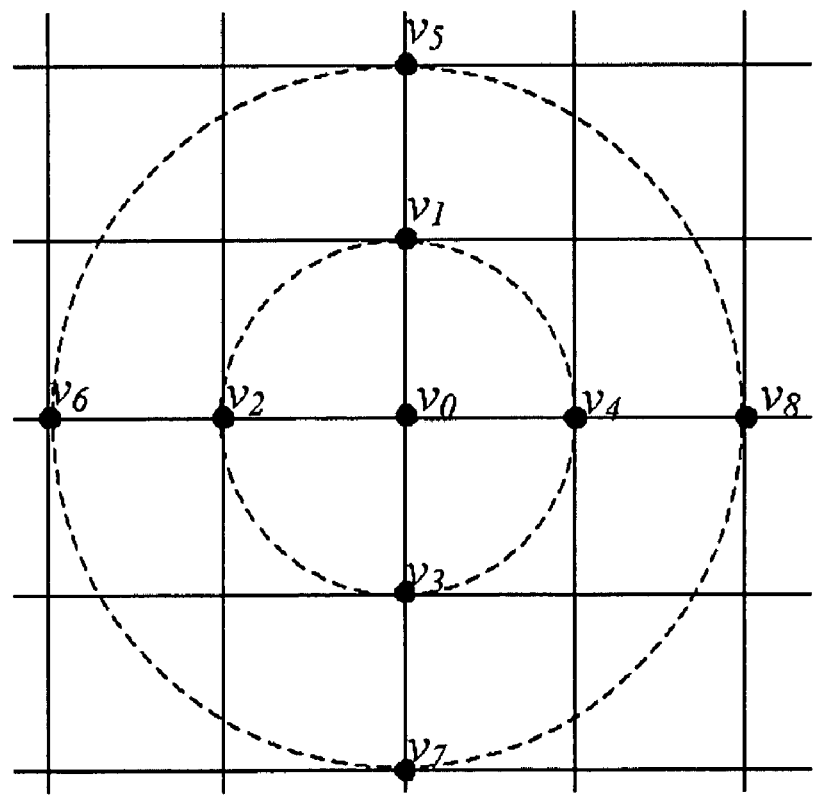
FIG. 10 graphically illustrates the configuration of nine electrode positions arranged in an array for use in 5-point and 9-point calculations, according to an embodiment of the present invention.

To improve the efficiency of the seizure control, the focus of the seizure activity is located prior to applying electrical stimulation. A unique method and device of the present invention can directly determine the depth, Z, and the X, Y locations of the electrical sources. This localization is utilized in locating the electrical activity origin of the neurological disorder. The methods for using EEG signals for localization are quite unique. The bioelectric neuro device preferably uses the pseudo-bipolar method to detect the depth of electric sources as described in the "detection sub-system". Or, concentric electrodes are configured in a form of 5-point or 9-point method for deeper depth detection. Conventional electrodes can also be arranged to approximate concentric electrodes for the purpose of depth detection. Considering the configuration shown in FIG. 10, where $v_0$, $v_1$ through $v_8$ are potentials measured by conventional disc electrodes placed at those locations respectively, the potential difference $P_5$ of the 5-point method is given as:

$$P_5 = v_0 - \frac{1}{4}(v_1 + v_2 + v_3 + v_4) \quad (1)$$

A variation of the 5-point method, the 9-point method is used for calculating the potential difference $P_9$ as:

$$P_9 = \frac{1}{2}\left(v_0 + \frac{1}{4}(v_1 + v_2 + v_3 + v_4)\right) - \frac{1}{4}(v_5 + v_6 + v_7 + v_8) \quad (2)$$

Figure 11:
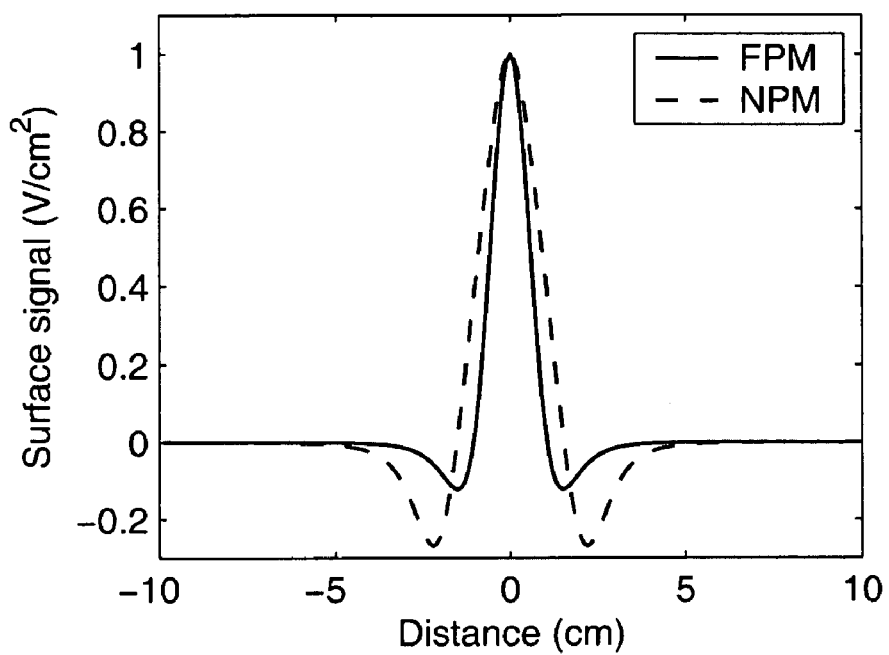
FIG. 11 graphically illustrates the difference between the electrical signals measured with the 5-point and the 9-point methods, with varying lateral positions of the dipole, according to an embodiment of the present invention.

The 9-point method has an attenuating effect similar to the 5-point method. However, because the nine electrodes cover a larger surface than the five electrodes, the attenuating effect tends to start at further distances from the source. This rather sluggish effect of the 9-point method can be seen from the comparison illustrated in FIG. 11. The slopes of the potentials from the 5-point and 9-point methods are different, as the slope of the 5-point method is steeper than the slope of the 9-point method. This difference in the response of the 5-point method and 9-point method for varying source location can be used to quantize the depth of a dipole source. As disc electrodes are not as effective at global signal rejection, concentric electrodes are used in the device and methods of the present invention to directly determine the depth of an electrical source.

Upon the determination of the depth of the electrical source with the multiple sized concentric electrodes, the X, Y location is defined. Solving equation (8) results in the location of P (X,Y) of a dipole. Here, it is assumed that the depth dz is known or measured through some method, such as the pseudo-bipolar difference method. The potentials measured by the electrodes are then used for localization of the electrical source in a multi-conductivity medium. It is expected that greater potentials will be observed on electrodes that are closer to the source than those farther.

The Laplacian potential at the center of the electrode can be approximated in a bipolar concentric ring electrode by equation (4):

$$LP1 \cong \frac{4}{(2r_o)^2}\{V_{oring1} - V_{disc1}\} \quad (4)$$

where, $V_{disc1}$ is the potential on the disc electrode, $V_{oring1}$ is the potential on the outer ring, $r_o$ is the radius of outer ring, and LP1 is the calculated Laplacian potential using the bipolar electrode. The tri-polar concentric Laplacian potential has previously been proven by the inventor to be approximated by equation (5):

$$LPN1 \cong \frac{1}{3r_o^2}\{16(V_{oring1} - V_{disc1}) - (V_{mring1} - V_{disc1})\} \quad (5)$$

where, $V_{disc1}$ is the potential on the disc electrode, $V_{mring1}$ is the potential on middle ring, $V_{oring1}$ is the potential on outer ring, $r_o$ is the radius of outer ring, and LPN1 is the calculated Laplacian potential for the tri-polar electrode.

Figure 12:
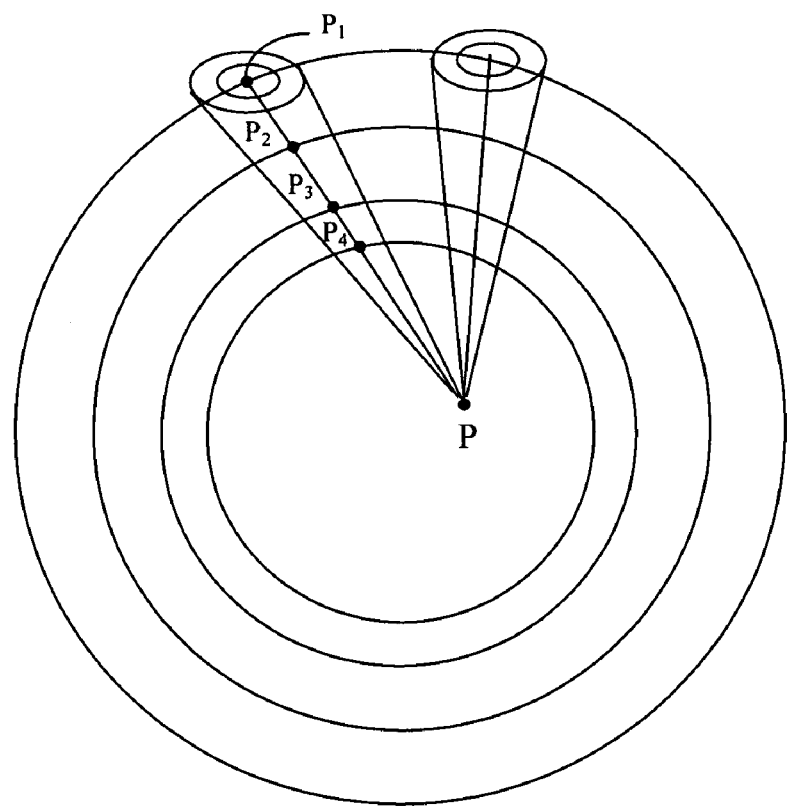
FIG. 12 is a 2-dimensional representation of a 'four concentric spheres' head model, according to an embodiment of the present invention, While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

The potential on the electrodes is given by equation (6). The distance of the dipole from the center of the sphere is taken as R. Referring to FIG. 12, $R \leq R_4$, and the line joining the dipole at position P and the electrode disc $P_1$ cuts the inner sphere (with radius $R_4$) at position $P_4$ (in the direction of $PP_1$) and similarly intersects the other two spheres at positions $P_3$ and $P_2$, respectively. Then, the potential on the surface electrode due to a dipole at position P is given as:

$$V_{PE1} = \frac{q}{4\pi}\left[\frac{dz_4}{\sigma_4(PP_4)^3} + \frac{dz_3}{\sigma_3(P_4P_3)^3} + \frac{dz_2}{\sigma_2(P_3P_2)^3} + \frac{dz_1}{\sigma_1(P_2P_1)^3}\right] \quad (6)$$

where, $V_{PE1}$ is the potential on the electrode, and $PP_4$ is the distance between positions P and $P_4$. Similarly, $P_4P_3$, $P_3P_2$, $P_2E_1$ are the distances between each of those points, and $dz_4$ is the difference between the z-coordinate of P and $P_4$. Similarly, $dz_3$ is between $P_4$ and $P_3$, $dz_2$ is between $P_3$ and $P_2$, and $dz_1$ is between $P_2$ and $P_1$.

The Laplacian potential for bipolar and tripolar electrode configurations is calculated by equations (4) and (5) and is represented in equation (8) as exp, and the analytical Laplacian of the surface potentials is calculated using equation (7) and is represented in equation (8) as cal.:

$$LPN_1^{cal} = \frac{\partial^2 V_{PE1}}{\partial X_d^2} + \frac{\partial^2 V_{PE1}}{\partial Y_d^2} \quad (7)$$

where, $LPN_1^{cal}$ is the calculated Laplacian Potential and $V_{PE1}$ is the potential on the disc given by equation (6). The localization is performed using equation (8)

$$\begin{pmatrix} X_d \\ Y_d \end{pmatrix}^{(I+1)} = \begin{pmatrix} X_d \\ Y_d \end{pmatrix}^{(I)} + (A^T A)^{-1} A^T \left(\overline{(LPN)}^{exp} - \overline{LPN}^{cal}\right) \text{ where,} \quad (8)$$

$$\begin{pmatrix} X_d \\ Y_d \end{pmatrix}^{(I+1)}$$

is the localized position of the dipole due to iteration (I+1), and matrix $A^T$ is the transpose of matrix A given as:

$$A^T = \begin{bmatrix} \frac{\partial LPN_1^{cal}}{\partial X_d} & \frac{\partial LPN_2^{cal}}{\partial X_d} & \frac{\partial LPN_3^{cal}}{\partial X_d} \\ \frac{\partial LPN_1^{cal}}{\partial Y_d} & \frac{\partial LPN_2^{cal}}{\partial Y_d} & \frac{\partial LPN_3^{cal}}{\partial Y_d} \end{bmatrix} \quad (9)$$

Of course, the above description is for calculated potentials in a computer model. In a real system, the potentials on the electrodes are automatically measured and used to directly solve the X,Y position with equation 8 and depth Z using the pseudo-bipolar method or some other method.

Another method for localizing the depth of an electrical source involves a transfer function. It is generally known that the potential measured at the surface, or away from the source, depends on the electrical source dipole moment and the position of the electrical source in the volume conductor. It is also known that the potentials measured, whether on the surface or within a volume conductor, also depend on the electrode's dimensions and shape.

There are many expressions that relate the surface potential to the electrode dimensions and shapes or to the position in a plane parallel to the surface. However, here is no record of any analytical expression that takes into account the 3D position of an electrical source and the shape and dimension of the electrode system at once.

As applicable to the present invention, an analytical expression that gives the potential measured by a disc electrode on the surface of a volume conductor due to a radial dipole inside a volume conductor is defined as:

$$\iint_{Disc} \phi_R = \frac{q}{4\pi^2 r_d^2 \sigma} \qquad (10)$$

$$\sqrt{\frac{r_d}{x_p}} \left[ \text{Log} \left[ \frac{-\sqrt{\frac{r_d}{x_p}(x_p + y_p)} + \sqrt{z_p^2 - rx_p + x_p^2 + (r_d - y_p)^2}}{\sqrt{\frac{r_d}{x_p}(x_p - y_p)} + \sqrt{z_p^2 - rx_p + x_p^2 + (r_d - y_p)^2}} \right] + \right.$$

$$\left. i\text{Log} \left[ \frac{-i\sqrt{\frac{r_d}{x_p}(x_p + y_p)} + \sqrt{z_p^2 - rx_p + x_p^2 + (r_d - y_p)^2}}{i\sqrt{\frac{r_d}{x_p}(x_p - y_p)} + \sqrt{z_p^2 - rx_p + x_p^2 + (r_d + y_p)^2}} \right] \right],$$

$$x_p \neq 0$$

$$\iint_{Disc} \phi_R = 0, \; x_p = 0$$

wherein, $\Phi$ is the potential measured at the surface, q is the charge of the dipole, (xp, yp, d) is the location of the dipole, $\sigma$ is the conductivity of the material of volume conductor, and r is the radius of the disc.

This equation can be extended easily to determine the potential as measured due to rings concentric to this disc electrode. Therefore, this expression for the disc and multiple rings combined together gives the depth perception, which is not possible by any other expression disclosed in the prior art.

As illustrated in FIG. 1 and FIG. 3, the detection sub-system has the built-in capability and the ability to receive new detection algorithms for detection of neurological disorders. There are many types of algorithms generally disclosed for this purpose, and they can be utilized by this detection sub-system. The use of the concentric electrodes with these detection algorithms should improve the algorithm efficiency, as the concentric electrodes have been shown to possess significant signal detection advancements over conventional electrodes.

A. Detection and Localization of Epileptic Activity

The first task of controlling an epileptic seizure is to know that it is occurring. This can be determined by some means external to, or by the bioelectric neuro device, e.g., seizure fibrillator. Preferably, the seizure is identified as it occurs; but it is more preferable that the seizure is identified before it occurs. An algorithm can be employed to identity pre-seizure activity. A hallmark of seizure-related brain activity is the appearance of signals comprising large changes in voltage values (i.e., spikes) in an EEG signal profile. Such spikes can arise by hyper-synchronization of brain activity and will quantitatively exceed those voltage measurements associated with normal, non-seizure related, brain activity. Therefore, in general the presence of a seizure can be identified by the presence of voltage spikes in an EEG signal profile.

In one embodiment, a seizure detection sub-system of a seizure fibrillator detects the presence of a seizure by comparing incoming EEG signals, which can be bandpass filtered to predetermined levels, with a predetermined threshold value or other pattern of brain activity associated with an epileptic seizure or condition. The seizure detection sub-system can employ standard circuitry and/or software to analyze incoming data and perform comparisons between incoming data and the seizure detection algorithm.

A seizure detection algorithm can be adapted to "learn" specific characteristics of a subject's brain activity before, during, and even after the occurrence of an epileptic seizure. In this way, a seizure detection algorithm can store one or more parameters, which are monitored during an epileptic seizure of a subject. At a later time, after the seizure has been controlled, the seizure detection algorithm incorporates the data into the algorithm itself. Preferably, when a later seizure occurs, or is predicted to occur, the seizure detection algorithm recognizes the onset of the seizure, based on measured data, and counteracts the seizure at an early point in time. It is preferable that a seizure detection algorithm be adapted to evolve over time in such a fashion as to make the algorithm more effective at recognizing and preventing and/or controlling a seizure.

An operator can preset the seizure detection algorithm. This seizure detection algorithm can be set manually either before or after the final set up of the seizure fibrillator, via the operator's communication interface. Appropriate seizure detection algorithms will be apparent to those skilled in the art upon consideration of the present disclosure. The proper seizure detection algorithm can be altered and adapted as necessary, which can facilitate the detection sub-system improving over time, and thereby continually increasing the efficiency of seizure detection, which in turn may lead to a more efficient application of electrical stimulation. Over a longer period of time, this may result in a lowered seizure frequency and improved quality of life for the afflicted person(s). It is preferable that a seizure detection algorithm be adapted to evolve over time in such a fashion as to make the algorithm more effective at recognizing and preventing and/or ameliorating a seizure.

B. Detection and Localization of Pain

It should be understood that multiple methods may be used to determine the site(s) where the electrode(s) may need to be located in order to control the pain, such as headaches. Because the location of headache pain will vary from patient to patient, the precise location (or locations) of electrode(s) placement should be determined on an individual basis. Stimulation of the electrode(s) is preferably performed at the time of the diagnosis to identify the optimal stimulation site or sites for maximum pain relief. The bioelectric neuro device can be controlled by the operator, who may be a physician, therapist, or even by the patient, on a self-administered dosage as necessary.

The hardware and methods described previously for detection and localization of epileptic activity are generally similar to those used for detection and localization of pain. There are certain electroencephalographic patterns evident for different types of pain. Empirical databases can be assembled for persons suffering from said manifestations, and the data can be used comparatively to determine if a patient's electroencephalogram matches any of the manifestations in the database. If a match is found, an appropriate therapy can be provided to alleviate the pain. Stimulation at particular areas may be used to help localize and diagnose specific types of pain originating from specific locations.

The methods of the present invention can be used to treat pain that may be caused by a variety of conditions, including, but not limited to, migraine headaches, which including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-lumbar puncture headache; low cerebro-spinal fluid pressure headache; chronic migraneous neuralgia, cervical headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder (such as atriovenous malformation); arthritis pain in the spine; reflex sympathetic dystrophy, cervicalgia, glossodynia, carotidynia; cricoidynia; otalgia due to middle ear lesion; gastric pain; sciatica; maxillary neuralgia; laryngeal pain, myalgia of neck muscles; trigeminal neuralgia (sometimes also termed tic douloureux); temporomandibular joint disorder; atypical facial pain; ciliary neuralgia; paratrigeminal neuralgia (also referred to as Raeder's syndrome); musculoskeletal neck pain; petrosal neuralgia; Eagle's syndrome; idiopathic intracranial hypertension; orofacial pain; myofascial pain syndrome involving the head, neck, and shoulder; paratrigeminal paralysis; sphenopalatine ganglion neuralgia (also referred to as lower-half headache, lower facial neuralgia syndrome, Sluder's neuralgia, and Sluder's syndrome); carotidynia; Vidian neuralgia; and causalgia; or any combination thereof.

C. Detection and Localization of Other Neurological Disorders

The hardware and methods described previously for detection and localization of epileptic activity are generally similar to those used for detection and localization of other neurological disorders. For specific movement disorders, it may be appropriate to incorporate means for tremor detection, which can use various types of algorithms to detect an EEG signature or other signature pertaining to the movement disorder. For other types of neurological disorders, there is evidence that certain electroencephalographic patterns may be evident. Empirical databases can be assembled for persons suffering from said manifestations and the data can be used comparatively to determine whether the patient's electroencephalogram matches any of the neurological disorder manifestations in the database. If a match is found, an appropriate therapy can be provided to alleviate the neurological disorder. Stimulation at particular areas may be used to help localize and diagnose specific types of neurological disorder originating from specific locations by blocking pain from certain areas.

The methods of the present invention can be used to detect and localize a variety of neurological disorders, including but not limited to, neurologic diseases such as Parkinson's disease, Huntington's disease, Parkinsonism, rigidity, hemiballism, choreoathetosis, akinesia, bradykinesia, hyperkinesia, other movement disorder such as dystonia, cerebropalsy, essential tremor, and hemifacial spasms, epilepsy, or generalized or partial seizure disorder, Alzheimer's disease, and Pick's disease; psychiatric diseases, such as depression, bipolar disorder, anxiety, phobia, schizophrenia, multiple personality disorder; psychiatric disorders, such as substance abuse, attention deficit hyperactivity disorder, impaired control of aggression, or impaired control of sexual behavior; other neurological conditions, such as those related to headaches; and concussions, post-concussive syndrome, stress, migraines, chronic headaches; and cerebrovascular diseases, such as atherosclerosis, cerebral aneurysm, stroke, cerebral hemorrhage; or any combination thereof 3.2 Treatment and Prevention of Neurological Disorders The bioelectric neuro device of the present invention may be used to treat and/or prevent neurological disorders. This involves the application of stimulation, alone or in combination with a sensory input, to a patient to elicit a response as a treatment. The sensory input may include physical manifestations, such as vibration, other electrical signals not directed to brain tissue (for example, somatosensory stimulation resulting in a scalp twitch or sensation in the scalp or other part of the body), light flashes, sound pulses, etc. Other types of stimulation, e.g., via drug delivery, may also be provided on demand from the detection sub-system.

The stimulation parameter generation algorithm residing in the stimulation controller 115*b* determines to which electrodes that electrical stimulation shall be provided in order to reach the source, if stimulation is necessary. The stimulation parameter generation algorithm instructs the electrode arbiter 111 to effectuate this task.

A. Treatment and Prevention of Epilepsy

A pilot study by the inventors showed that the use of electrical stimulation in the control of seizure activity of the brain is possible. This idea can easily be modified to create an internalized seizure cessation apparatus. Alternatively, both external and internal components can be used.

The bioelectric neuro device of the present invention, e.g., a seizure fibrillator is used for the treatment and/or prevention of epilepsy. In its most basic variation, the seizure fibrillator provides neurostimulation in a first mode, non-responsive (i.e., programmed) stimulation, which modulates neural activity, providing neural desynchronization in the brain resulting in a reduction of neurological disorder events. The non-responsive stimulation and the responsive stimulation may be delivered from the same electrode, but they also may be delivered from separate electrodes connected to the same seizure fibrillator. The location of the electrode(s) for stimulation is preferably such that stimulation targets the focus of the neurological disorder. However, this need not be the case.

Non-responsive stimulation typically is made up of low intensity, short duration pulses delivered at a rate in the range of from about 10 Hz to about 250 Hz. The pulses may be square pulses, or may have other morphologies, such as exponential, sinusoidal, triangular, and trapezoidal. The pulses may be voltage controlled, or preferably, current controlled. Generally, the pulses will be biphasic to achieve charge balance, but waveforms having a net DC component may also have utility if used in conjunction with appropriate electrodes. To reduce the likelihood of the stimulation promoting epileptogenesis, high frequency stimulation having a primary frequency in the range of from about 10 Hz to about 250 Hz (or pulse-to-pulse intervals of about 100 milliseconds to about 4 milliseconds) may be used for a duration of about 15 sec. to about 30 min. or longer, if necessary, delivered from the same electrode as the responsive stimulation, or from a different electrode(s). The stimulation may be delivered on a scheduled basis, on an as needed basis, or per the patient's mandates.

The electrode 120 of the bioelectric neuro device is preferably controllable to produce output stimulating signals that can be varied in voltage, frequency, pulse width, current, and intensity. Further, the electrode 120 is preferably controllable such that the controller may produce both positive and negative current flow from the electrode, stop current flow from the electrode, or change the direction of current flow from the electrode. The electrode 120 preferably has the capacity for variable output, such as complex exponential waveforms, and linear output. While it is anticipated that a signal generator will typically be used to control the electrode 120, it should be understood that any device or combination of devices may be used to allow the operator to adjust the electrode as described herein.

It is recommended that the application of stimulus from the electrode 120 and adjustments of the electrode parameters as described herein are performed, preferably, under the supervision and guidance of a physician. However, the operator may be a technician or the patient, who could activate the electrode(s) 120 to stimulate the desired region. While it may be possible to configure the electrode(s) 120 and its controller such that the patient could alter the parameters of the electrode(s) stimulus without supervision by a physician, this would not be recommended, as the patient may not have sufficient knowledge to avoid dangers associated with misapplication of the methods disclosed herein.

In one embodiment, the electrode(s) 120 are connected to a power source (such as a battery or pulse generator) which provides the energy source for the electrical stimulation. The electrode(s) 120 may be mono-polar, or multi-polar. However, the use of a multi-polar electrode is preferred. Unipolar stimulation typically utilizes a pole and a reference electrode, and requires relatively high amounts of current. Bipolar stimulation utilizes adjacent poles with current flowing from the negative pole (cathode) to the positive pole (anode), and causes depolarization of nervous tissue at current levels lower than with unipolar stimulation. Whereas, multi-polar stimulation can have multiple anodes and cathodes, where one electrode could actually be an anode relative to another electrode and a cathode relative to a more positive electrode. Very complex electric fields can be established within the biological tissue with multi-polar electrode configurations, which may have benefits in desynchronizing epileptiform activity.

In one embodiment, the electrode 120 is controlled to produce an electronic current for the application of stimulation. Preferably, the current will comprise relatively high frequency pulses, and may possess a low frequency amplitude or frequency modulation. The exact parameters for the electrical stimulation of the electrodes are likely to vary by patient; however, based upon data known for stimulations performed on the brain, parameters suitable for use herein are: a frequency in the range of from about 0.1 Hz to about 2500 Hz, preferably in the range of from about 10 Hz to about 250 Hz, and a pulse width in the range of from about 10 microseconds to about 10 seconds, preferably in the range of from about 50 microseconds to about 250 microseconds, a voltage amplitude in the range of from about 500 mv to about 2K volts, preferably in the range of from about 30 volts to about 100 volts, and a current amplitude in the range of from about 0.01 mA to about 1 amp (A), preferably in the range of from about 5.0 mA to about 50 mA. Shorter pulse widths are preferred for safety considerations. In another embodiment, high frequency bursts of current are produced on top of an underlying low frequency continuous stimulus. Preferably, the electrode is associated with a programmable controller, which may be utilized to produce continuous, scheduled, or episodic, responsive stimulation. In another embodiment, the programmable controller is utilized to gradually increase stimulation to desired maximum levels. Alternatively, a programmable controller is utilized to immediately produce stimulation at the desired maximum level or to perform any number of intermediate steps to reach the maximum level.

In one embodiment of the present invention, bioelectric neuro device 100 is utilized for prevention of neurological events. This method involves the detection and analysis of brain's electrical activity to detect epileptiform activity or to detect such impending activity. If the epileptiform activity is present or is impending, responsive stimulation may be initiated. The results of the epileptiform activity analysis may also be used to modify the parameters of the non-responsive stimulation to improve the suppression of seizures or other undesirable neurological events. The responsive stimulation is initiated when an analysis of the EEG, or other signals, shows an impending or existent neurological event, such as epileptiform activity. When the seizure onset is detected and electrical stimulation is applied, the seizure is pre-empted. If all seizures are pre-empted, by definition, epilepsy is prevented.

In another embodiment, stimulation is applied at intermittent or preset periods to prevent epilepsy. Electrical stimulation may be applied on an as needed basis by the epilepsy sufferer to prevent epileptic activity. If the epilepsy sufferer feels an aura, he or she may want to turn the electrical stimulation on to pre-empt the seizure. The VNS system allows the patient to manually turn the stimulation on as needed. Lasting affects have been reported due to the use of electric stimulations for seizures, implying that using stimulation for brief periods may have prolonged benefit, such as using it prior to retiring to bed.

In another embodiment, the parameters (e.g., electrode(s) used, morphology of the stimulating signal, number of pulses or cycles of the stimulating signal, amplitude, pulse-to-pulse interval or frequency of the stimulating signal, duration of the stimulating signal, etc.) of the responsive stimulation are varied. The variation of the parameters may be based either upon a preprogrammed sequence or based upon some characteristic of the detected abnormal neural activity. Additionally, the parameters of the responsive stimulation are varied between different episodes of spontaneous abnormal neural activity to minimize the tendency of the stimulation itself to predispose the brain to epileptogenesis (also known as "kindling"). Analysis of the electrical activity of the brain can continue while stimulation is applied by analyzing electrodes that are not being stimulated to determine whether the stimulation has had its desired effect.

B. Treatment and Prevention of Other Neurological Disorders

The bioelectric neuro device of the present invention, e.g., a neurostimulator, is used to for the treatment and/or prevention of other neurological disorders. In one embodiment of the present invention, a neurostimulator provides varied stimulus intensity. The stimulation may be activating, inhibitory, or a combination of activating and inhibitory, and the disorder is neurologic or psychiatric.

In the basic mode of operation, neurostimulator 100 is used for applying non-responsive stimulation, similar as for epilepsy. The stimulation may be applied at predetermined time intervals as a preventative measure, or applied in response to detection of a neurological disorder event. For a specific neurological disease, such as for Parkinson's disease, stimulation is applied to disrupt the neurological activity that causes the manifestation of the disease. In deep brain stimulation, bilateral stimulation of the thalamus or globus pallidus are typically targeted. The stimulation parameters preferable for use herein are pulses in the range of from about 100 Hz to about 200 Hz, and pulse width in the range of about 50 usec to about 100 usec, with a large proportion of on-to-off times. These stimulation techniques can all be performed non-invasively.

Both non-responsive and responsive modes can be beneficial for prevention of neurological disorders. As electrical stimulation, such as electroconvulsive therapy, is known to cause neurogenesis, applying non-responsive neurostimulation at preset intervals, or even occasionally, may act as a preventive maintenance mechanism for a patient's neurological system.

C. Treatment and Prevention of Pain

The pathophysiology creating the described pain is not often fully clear. For example, in the case of migraine headaches, a number of neurological and vascular events have been identified which take place prior to the onset of migraine pain. Research shows that a primary neuronal process triggers changes in dural vessels, which induces sterile inflammation that leads to activation of the trigeminal nucleus and the onset of head pain. Specifically, cortical depression suppresses cortical neuronal activity in the patient, followed by activation of migraine centers in the brain stem, and the start of perivascular inflammation. Dilation and constriction of cranial blood vessels may also occur. As the main pain sensitive structures in the brain are the large blood vessels, the venous sinuses, and the meninges, it is believed that the perivascular inflammation may be the primary cause of head pain felt by migraine sufferers in many cases.

The large cerebral vessels, pial vessels, large venous sinuses and the surrounding dura are innervated by a plexus of nerve fibers (which are mostly unmyelinated), that arise from the trigeminal ganglion, and the posterior fossa, that arise from the upper cervical dorsal nerve roots. This nerve fiber plexus is in the form of a sheath that wraps around the dural sinuses and blood vessels. The nerve fiber plexus contains many inflammatory mediators. When the trigeminal ganglion is stimulated, the inflammatory mediators are released, causing sterile neurogenic inflammation of the perivascular space.

The bioelectric neuro device of the present invention can be utilized to localize electrical stimulation of the venous sinuses and adjacent dura or falx cerebri of the superior sagittal sinus, confluence of sinuses, occipital sinus, sigmoid sinus, transverse sinus; straight sinus; inferior sagittal sinus, or a combination thereof, using one or more electrodes on or under the scalp, or electrodes that are surgically implanted on, in, or near the brain, or any combination thereof, for treatment of a number of medical conditions.

In one embodiment of the present invention, the bioelectric neuro device 100 is used to disrupt neurogenic inflammation by stimulating the nerve fibers innervating the dural sinuses. This is accomplished by using the electrodes 120 to deliver electrical stimuli to one or more of the dural venous sinuses and/or the surrounding dura and falx cerebri in order to cancel signals passing through the nerve fibers, which stimulate the neurogenic inflammation. This may occur due to the stimulation of neurons, which act to suppress the signals, or which in turn activate other neurons that act to suppress the signals, the stimulation of neurons to directly inhibit the neurons, which may stimulate the neurogenic inflammation, or a combination of the foregoing. Such stimulation may also act to disrupt the process by which inflammatory mediators, such as vasoactive peptide, are released from the afferent nerve fibers. The electrodes need not be in direct contact with the nerve fibers, only the stimulation current needs to contact the nerve fibers.

In one embodiment, the treatment method provides pain relief by disrupting pain signals transmitted through the nerve fibers, even with neurogenic inflammation. Once nerves are sensitized, due to neurogenic inflammation, they act as transducers and change chemical pain signals into electrical pain signals. The nerves then carry the generated electrical pain signals back to the trigeminal ganglion and then to the brainstem and brain pain centers, resulting in the perception of pain by the patient. The electrical stimuli applied by electrodes 120 to reach one or more of the dural venous sinuses and/or the surrounding dura and falx cerebri can influence and modulate the transduction of the chemical pain signals into electrical pain signals, as well as suppress or prevent the transmission of the electrical pain signals.

The methods of the present invention also pertain to the use of the bioelectric neuro device to deliver electrical stimulation via concentric electrodes in combination with other peripheral stimulation techniques, such as drugs and/or sound.

While the above description of the invention has been presented in terms of a human subject (patient), it is appreciated that the invention may also be applicable to treating other mammals.

As noted above, the present invention is applicable to devices for detecting, preventing, and/or treating neurological disorders, and methods related thereto. The present invention should not be considered limited to the particular embodiments described above, but rather should be understood to cover all aspects of the invention as fairly set out in the appended claims. Various modifications, equivalent processes, as well as numerous structures to which the present invention may be applicable will be readily apparent to those skilled in the art to which the present invention is directed upon review of the present specification. The claims are intended to cover such modifications and devices.

We claim:

1. A method of detecting brain electrical patterns indicative of a neurological event comprising
    a) positioning at least two electrodes on the scalp or between the scalp and the cranium of a mammal;
    b) monitoring with said at least two electrodes patterns of brain electrical patterns of the mammal's brain to identify the presence or onset of a neurological event;
    c) identifying the location of the brain electrical patterns indicative of a neurological event;
    wherein each of said at least two electrodes have at least two poles comprising conductive elements configured concentrically and wherein each of said at least two electrodes is positioned wholly outside the cranium.

2. A method to modify brain electrical patterns indicative of a neurological event comprising
    a) positioning at least two electrodes on the scalp or between the scalp and the cranium of a mammal;
    b) monitoring with said at least two electrodes patterns of brain electrical patterns of the mammal's brain to identify the presence or onset of a neurological event;
    c) identifying the location of the brain electrical patterns indicative of a neurological event;
    d) applying electrical stimulation to beneficially modify said brain electrical patterns;
    wherein the stimulation is applied from at least one of said at least two electrodes;
    wherein each of said at least two electrodes have at least two poles comprising conductive elements configured concentrically; and wherein each of said at least two electrodes is positioned wholly outside the cranium.

3. The method of claim 2, wherein the electrical stimulation is applied in the form of sustained current, pulsed current, specific pulse pattern, sustained voltage, pulsed voltage, or any combination thereof.

4. The method of claim 2, wherein the electrical stimulation is applied at a frequency in the range of from about 0.1 Hz to about 2500 Hz, a pulse width in the range of from about 10 μsec to about 10 sec, and for a duration of from about 15 sec to about 30 min.

5. The method of claim 2, wherein the electrical stimulation is applied at a frequency in the range of from about 10 Hz to about 250 Hz, a pulse width in the range of from about 50 μsec to about 250 qsec, and for a duration of from about 30 sec to about 5 min.

6. The method of claim 2, wherein the electrical stimulation is applied at a voltage in the range of from about 500 mV to about 2 kV, or current in the range of from about 0.01 mA to about 1000 mA.

7. The method of claim 2, the electrical stimulation is applied at a voltage in the range of from about 30 V to about 100 V, or current in the range of from about 5 mA to about 75 mA.

8. The method of claim 2, wherein the neurological event is associated with a disease selected from the group consisting of epilepsy, Parkinson's Disease, Huntington's disease, Alzheimer's disease, Pick's disease, Parkinsonism, rigidity, hemiballism, choreoathetosis, dystonia, akinesia, bradykinesia, hyperkinesia, depression, bipolar disorder, anxiety, phobia, schizophrenia, multiple personality disorder, substance abuse, attention deficit hyperactivity disorder, eating disorder, impaired control of aggression, impaired control of sexual behavior, headache, migraine, concussion, post-concussive syndrome, and stress-related disorder.

9. The method of claim 8, wherein said neurological event is associated with epilepsy.

10. The method of claim 9, wherein said neurological event is indicative of the onset of a seizure.

11. The method of claim 2 wherein said monitoring is with five or nine electrodes.

12. The method of claim 2, wherein said at least one electrode is positioned on the scalp.

13. The method of claim 2, wherein said at least one electrode is positioned below the scalp but outside the cranium.

14. The method of claim 2, wherein at least one electrode has at least three poles comprising conductive elements configured concentrically.

15. The method of claim 14, wherein at least one electrode consists of three poles comprising conductive elements configured concentrically.

16. The method of claim 14, wherein the gap between the conductive elements configured concentrically is approximately equal to the width of the conductive elements.

* * * * *